(12) United States Patent
Adachi et al.

(10) Patent No.: US 10,559,761 B2
(45) Date of Patent: Feb. 11, 2020

(54) LIGHT-EMITTING MATERIAL, AND ORGANIC ELECTROLUMINESCENT DEVICE

(71) Applicants: Hodogaya Chemical Co., Ltd., Tokyo (JP); Kyushu University, National University Corporation, Fukuoka-shi (JP)

(72) Inventors: Chihaya Adachi, Fukuoka (JP); Takehiro Takahashi, Tokyo (JP)

(73) Assignees: Kyulux, Inc., Fukuoka (JP); Hodogaya Chemical Co., Ltd., Tokyo (JP)

( * ) Notice: Subject to any disclaimer, the term of this patent is extended or adjusted under 35 U.S.C. 154(b) by 161 days.

(21) Appl. No.: 15/556,801

(22) PCT Filed: Mar. 1, 2016

(86) PCT No.: PCT/JP2016/056155
§ 371 (c)(1),
(2) Date: Sep. 8, 2017

(87) PCT Pub. No.: WO2016/143589
PCT Pub. Date: Sep. 15, 2016

(65) Prior Publication Data
US 2018/0047915 A1    Feb. 15, 2018

(30) Foreign Application Priority Data
Mar. 9, 2015   (JP) .................. 2015-046011

(51) Int. Cl.
*C07D 403/14* (2006.01)
*H01L 51/00* (2006.01)
(Continued)

(52) U.S. Cl.
CPC ........ *H01L 51/0072* (2013.01); *C07D 403/14* (2013.01); *C09K 11/02* (2013.01);
(Continued)

(58) Field of Classification Search
None
See application file for complete search history.

(56) References Cited

U.S. PATENT DOCUMENTS 8,530,063 B2    9/2013  Kim et al.
9,334,260 B2    5/2016  Parham et al.
(Continued)

FOREIGN PATENT DOCUMENTS

CN    102391308 A    3/2012
CN    102770427 A    11/2012
(Continued)

OTHER PUBLICATIONS

Uoyama et al., Nature 492, Dec. 13, 2012, pp. 234-240.*
(Continued)

*Primary Examiner* — Vu A Nguyen
(74) *Attorney, Agent, or Firm* — Locke Lord LLP; James E. Armstrong, IV; Nicholas J. DiCeglie, Jr.

(57) ABSTRACT

To provide a light-emitting material containing a compound having a high excitation triplet level, particularly a host material of a light emitting layer, as a material for an organic electroluminescent device with high efficiency, and also to provide an organic electroluminescent device with high efficiency and high luminance by using the material. A light-emitting material containing a compound having a carbazole ring structure represented by the following general formula (1), and an organic electroluminescent device containing a pair of electrodes and one layer or plural layers including at least a light emitting layer intervening between the electrodes, the light emitting layer containing as a constitutional material thereof the light-emitting material.

(Continued)

[Chemical Formula 1]

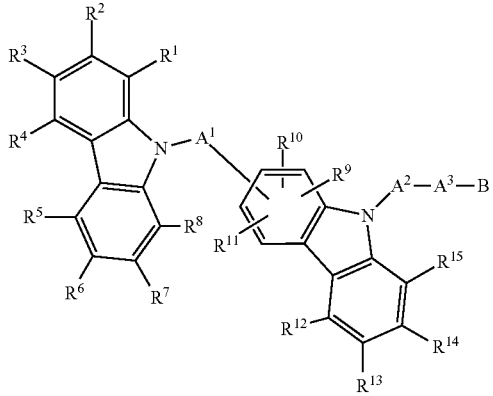

(1)

12 Claims, 5 Drawing Sheets

(51) Int. Cl.
  *H01L 51/50* (2006.01)
  *C09K 11/06* (2006.01)
  *C09K 11/02* (2006.01)
(52) U.S. Cl.
  CPC .......... *C09K 11/06* (2013.01); *H01L 51/0067* (2013.01); *H01L 51/50* (2013.01); *C09K 2211/1018* (2013.01); *H01L 51/5012* (2013.01); *H01L 51/5016* (2013.01)

(56) References Cited

U.S. PATENT DOCUMENTS

| 2012/0205636 A1 | 8/2012 | Kim et al. |
| 2012/0223276 A1 | 9/2012 | Parham et al. |
| 2013/0285030 A1 | 10/2013 | Yu et al. |
| 2015/0126736 A1 | 5/2015 | Cho et al. |
| 2015/0159084 A1 | 6/2015 | Cho et al. |
| 2015/0171342 A1 | 6/2015 | Jung et al. |
| 2015/0266863 A1 | 9/2015 | Dyatkin et al. |
| 2015/0349273 A1 | 12/2015 | Hung et al. |
| 2016/0204359 A1 | 7/2016 | Lee et al. |
| 2017/0117485 A1 | 4/2017 | Cho et al. |

FOREIGN PATENT DOCUMENTS

| CN | 104271702 A | 1/2015 | |
| CN | 104926805 A | 9/2015 | |
| CN | 105294658 A | 2/2016 | |
| JP | 2007-184348 A | 7/2007 | |
| JP | 2010-040830 A | 2/2010 | |
| JP | 2012-216801 A | 11/2012 | |
| JP | 2015-229677 A | 12/2015 | |
| KR | 2012-0092908 A | 8/2012 | |
| WO | 2010/004877 A1 | 1/2010 | |
| WO | 2011/049325 A2 | 4/2011 | |
| WO | 2011/057706 A2 | 5/2011 | |
| WO | 2012/091279 A1 | 7/2012 | |
| WO | 2013/089424 A1 | 6/2013 | |
| WO | 2013/165192 A1 | 11/2013 | |
| WO | WO-2013165192 A1 * | 11/2013 | ........... C07D 401/14 |
| WO | 2014/014310 A1 | 1/2014 | |
| WO | 2015/016498 A1 | 2/2015 | |
| WO | 2015142036 A1 | 9/2015 | |

OTHER PUBLICATIONS

Suzuki et al., Journal of Materials Chemistry C, 2015, 3, 1700-1706.*
SciFinder Search (Sep. 9, 2019).*
Supplementary European Search Report dated Jul. 2, 2018, issued for the European patent application No. 16761559.0.
International Search Report dated May 24, 2016, issued for PCT/JP2016/056155.
Office Action issued in correspoding Chinese Patent Application No. CN201680014437.8 (and its Japanese translation), dated May 27, 2019.

* cited by examiner

LIGHT-EMITTING MATERIAL, AND ORGANIC ELECTROLUMINESCENT DEVICE

TECHNICAL FIELD

The present invention relates to light-emitting materials for an organic electroluminescent device, suitable for an organic electroluminescent device, which is a preferred self-luminous device for various display devices, and to such organic electroluminescent devices. Specifically, this invention relates to light-emitting materials comprising compounds having a carbazole ring structure, and to organic electroluminescent devices (hereinafter also referred to as organic EL devices) using the materials.

BACKGROUND ART

The organic EL device is a self-luminous device and has been actively studied for their brighter, superior visibility and the ability to display clearer images in comparison with liquid crystal devices.

In 1987, C. W. Tang and colleagues at Eastman Kodak developed a laminated structure device using materials assigned with different roles, realizing practical applications of an organic EL device with organic materials. These researchers laminated an electron-transporting phosphor and a hole-transporting organic substance, and injected both charges into a phosphor layer to cause emission in order to obtain a high luminance of 1,000 cd/m² or more at a voltage of 10 V or less (refer to Patent Documents 1 and 2, for example).

To date, various improvements have been made for practical applications of the organic EL device. Various roles of the laminated structure are further subdivided to provide an electroluminescence device that includes an anode, a hole injection layer, a hole transport layer, a light emitting layer, an electron transport layer, an electron injection layer, and a cathode successively formed on a substrate, and high efficiency and durability have been achieved by the electroluminescence device (refer to Non-Patent Document 1, for example).

Further, there have been attempts to use triplet excitons for further improvements of luminous efficiency, and the use of a phosphorescence-emitting compound has been examined (refer to Non-Patent Document 2, for example).

Devices that use light emission caused by thermally activated delayed fluorescence (TADF) have also been developed. In 2011, Adachi et al. at Kyushu University, National University Corporation realized 5.3% external quantum efficiency with a device using a thermally activated delayed fluorescent material (refer to Non-Patent Document 3, for example).

The light emitting layer can be also fabricated by doping a charge-transporting compound generally called a host material, with a fluorescent compound, a phosphorescence-emitting compound, or a delayed fluorescent-emitting material. As described in the Non-Patent Document, the selection of organic materials in an organic EL device greatly influences various device characteristics such as efficiency and durability (refer to Non-Patent Document 2, for example).

Because phosphorescence-emitting compounds and delayed fluorescent-emitting materials undergo concentration quenching, a charge-transporting compound, or a host compound as it is generally called, is used to support the phosphorescence-emitting compounds or the delayed fluorescent-emitting materials by being doped with the phosphorescence-emitting compounds or the delayed fluorescent-emitting materials. The phosphorescence-emitting compounds or the delayed fluorescent-emitting materials so supported are called guest compounds.

4,4'-Di(N-carbazolyl)biphenyl (CBP) represented by the following formula is commonly used as the host compound (refer to NPL 4, for example).

[Chemical Formula 1]

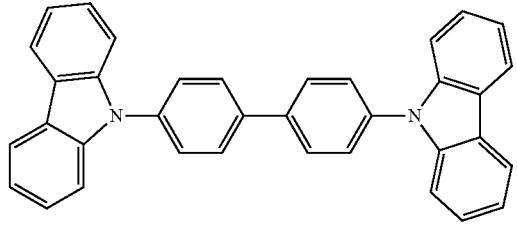

(CBP)

However, because of the low glass transition point (Tg) of 62° C. and high crystallinity, it has been indicated that CBP lacks stability in the thin-film state. The device characteristics are thus unsatisfactory in situations where heat resistance is needed such as in emitting light of high luminance.

Advances in phosphorescent device studies have promoted further understanding of the energy transfer process between the phosphorescent material and the host compound. Studies found that the host compound needs to have a higher excitation triplet level than the phosphorescent material in order to increase luminous efficiency.

The external quantum efficiency of a phosphorescent device remains at about 6% when the blue phosphorescent material FIrpic of the formula below is doped to CBP to provide the host compound of the light emitting layer. This is considered to be due to the lower excitation triplet level of CBP, 2.57 eV, than the excitation triplet level, 2.67 eV, of FIrpic, making it difficult for the FIrpic to sufficiently confine triplet excitons. This has been demonstrated by the temperature dependence of the photoluminescence intensity of a thin film produced by the doping of CBP with FIrpic (refer to NPL 5, for example).

It has been known that in the case where the delayed fluorescent-emitting materials are used, the excitation triplet level of the host compound needs to be higher than the excitation triplet level of the light-emitting material (refer to NPL 6, for example).

[Chemical Formula 2]

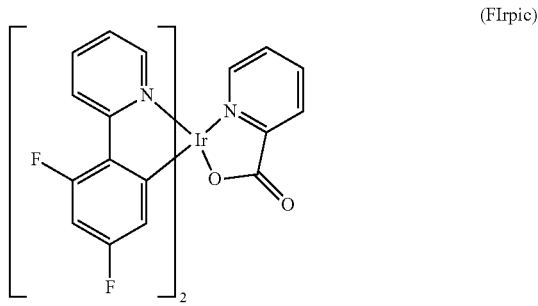

(FIrpic)

The host compound 1,3-bis(carbazol-9-yl)benzene (mCP) of the formula below is known to have a higher excitation triplet level than CBP. However, as with the case of mCP, mCP has a low glass transition point (Tg) of 55° C. and high crystallinity, and lacks stability in the thin-film state. The device characteristics are thus unsatisfactory in situations where heat resistance is needed such as in emitting light of high luminance (refer to NPL 5).

[Chemical Formula 3]

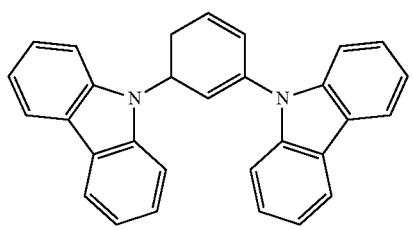

(mCP)

It has been found from the studies of host compounds of higher excitation triplet levels that doping an iridium complex to an electron transporting host compound or a bipolar transporting host compound can produce high luminous efficiency (refer to NPL 7, for example).

In an organic EL device, light emission is obtained in a light emitting layer through recombination of charges injected from both the electrodes, and for providing an organic EL device with high efficiency, a low voltage operation capability, and a long lifetime, by using a bipolar transporting host compound, a device excellent in carrier balance can be obtained, in which electrons and holes can be efficiently injected or transported to the light emitting layer, and can be efficiently recombined.

As described above, in order to improve the luminous efficiency of a phosphorescent device or a delayed fluorescent-emitting device in actual settings, a light-emitting-layer host compound is needed that has a high excitation triplet level, and high thin-film stability.

CITATION LIST

Patent Literature

PTL 1: JP-A-8-48656
PTL 2: Japanese Patent No. 3194657

Non Patent Literature

NPL 1: The Japan Society of Applied Physics, 9th Lecture Preprints, pp. 55 to 61 (2001)
NPL 2: The Japan Society of Applied Physics, 9th Lecture Preprints, pp. 23 to 31 (2001)
NPL 3: Appl. Phys. Let., 98, 083302 (2011)
NPL 4: Appl. Phys. Let., 75, 4 (1999)
NPL 5: Development and Evaluation Techniques for Organic EL Illumination Materials, p 102-106, Science & Technology, (2010)
NPL 6: Sci. Rep., 3, 2127 (2013)
NPL 7: Organic EL Display p 90, Ohm Electric, Ltd. (2005)
NPL 8: NATURE 492, 235 (2012)
NPL 9: Organic EL Symposium, the 1st Regular presentation prints, 19 (2005)

SUMMARY OF INVENTION

Technical Problem

An object of the invention is to provide as a material for an organic EL device with high efficiency, a light-emitting material containing a compound having a high excitation triplet level, and particularly a host material for a light emitting layer, and to provide an organic EL device with high efficiency and high luminance by using the material. Examples of the physical characteristics that the material to be provided by the invention should have include (1) the material contains a compound having a high excitation triplet level, (2) the material contains a compound having a bipolar transporting property, (3) the material is stable in a thin film state, (4) the material is excellent in heat resistance, and the like. Examples of the physical characteristics that the organic EL device to be provided by the invention should have include (1) the device has high luminous efficiency, (2) the device has a low light emission starting voltage, (3) the device has a low practical operation voltage, (4) the device has a long lifetime, and the like.

Solution to Problem

For achieving the aforementioned object, the present inventors, who have focused compounds having a heterocyclic structure such as a carbazole ring structure having a high hole transporting property and a triazine ring having a high electron transporting property, have chemically synthesized the compounds through compound design based on the excitation triplet level obtained by the theoretical calculation as an index, and have actually measured the excitation triplet level, and the inventors have thus found a light emitting material (host material) a compound having a carbazole ring structure having characteristics that are suitable for a light emitting device emitting delayed fluorescence. The inventors have experimentally produced various organic EL devices using the material and have earnestly evaluated the characteristics of the devices, and thus the invention has been completed.

(1) The invention relates to a light-emitting material containing a compound having a carbazole ring structure represented by the following general formula (1):

[Chemical Formula 4]

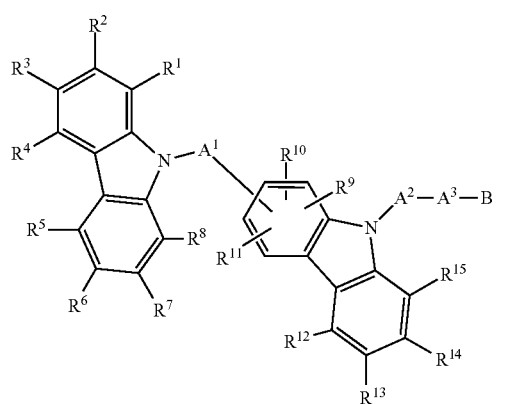

(1)

In the formula, $A^1$ and $A^2$ may be the same or different, and each represents a divalent group of a substituted or unsubstituted aromatic hydrocarbon or a divalent group of a substituted or unsubstituted condensed polycyclic aromatics; $A^3$ represents a divalent group of a substituted or unsubstituted aromatic hydrocarbon, a divalent group of a substituted or unsubstituted condensed polycyclic aromatics, or a single bond; B represents a substituted or unsubstituted aromatic heterocyclic group; and $R^1$ to $R^{15}$ may be the same or different, and each represents a hydrogen atom, a deuterium atom, a fluorine atom, a chlorine atom, cyano, nitro, linear or branched alkyl of 1 to 20 carbon atoms, that may have a substituent, cycloalkyl of 5 to 10 carbon atoms, that may have a substituent, linear or branched alkenyl of 2 to 20 carbon atoms that may have a substituent, linear or branched alkyloxy of 1 to 20 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, a substituted or unsubstituted aryloxy group, or a disubstituted amino group substituted with an aromatic hydrocarbon group, an aromatic heterocyclic group, or a condensed polycyclic aromatic group, and may bind to each other via a single bond, a substituted or unsubstituted methylene, an oxygen atom, or a sulfur atom, to form a ring.

(2) The invention relates to the light-emitting material according to the item (1), wherein in the general formula (1), $A^1$ represents phenylene.

(3) The invention relates to the light-emitting material according to the item (1) or (2), wherein in the general formula (1), $A^2$ represents phenylene.

(4) The invention relates to the light-emitting material according to any one of the items (1) to (3), wherein in the general formula (1), $A^3$ represents phenylene.

(5) The invention relates to the light-emitting material according to any one of the items (1) to (3), wherein in the general formula (1), $A^3$ represents a single bond.

(6) The invention relates to the light-emitting material according to any one of the items (1) to (3), wherein in the general formula (1), $A^3$ represents biphenylene.

(7) The invention relates to an organic EL device containing a pair of electrodes and one layer or plural layers including at least a light emitting layer intervening between the electrodes, the light emitting layer containing as a constitutional material thereof the light-emitting material according to any one of the items (1) to (6).

(8) The invention relates to the organic EL device according to the item (7), wherein the light-emitting material according to any one of the items (1) to (6) is used as a host material of the light emitting layer.

(9) The invention relates to the organic EL device according to the item (7) or (8), wherein the organic EL device emits delayed fluorescence.

Specific examples of the "aromatic hydrocarbon" or the "condensed polycyclic aromatics" in the "substituted or unsubstituted aromatic hydrocarbon" or the "substituted or unsubstituted condensed polycyclic aromatics" in the "divalent group of a substituted or unsubstituted aromatic hydrocarbon" or the "divalent group of a substituted or unsubstituted condensed polycyclic aromatics" represented by $A^1$, $A^2$, and $A^3$ in the general formula (1) include benzene, biphenyl, terphenyl, tetrakisphenyl, styrene, naphthalene, anthracene, acenaphthylene, fluorene, phenanthrene, indane, pyrene, perylene, fluoranthene, and triphenylene.

The "divalent group of a substituted or unsubstituted aromatic hydrocarbon" or the "divalent group of a substituted or unsubstituted condensed polycyclic aromatics" represented by $A^1$, $A^2$, and $A^3$ in the general formula (1) means a divalent group that results from the removal of two hydrogen atoms from the "aromatic hydrocarbon" or the "condensed polycyclic aromatics".

Specific examples of the "substituent" of the "substituted aromatic hydrocarbon" or the "substituted condensed polycyclic aromatics" in the "divalent group of a substituted or unsubstituted aromatic hydrocarbon" or the "divalent group of a substituted or unsubstituted condensed polycyclic aromatics" represented by $A^1$, $A^2$, and $A^3$ in the general formula (1) include a deuterium atom, cyano, nitro; halogen atoms, such as a fluorine atom, a chlorine atom, a bromine atom, and an iodine atom; linear or branched alkyls of 1 to 6 carbon atoms, such as methyl, ethyl, n-propyl, isopropyl, n-butyl, isobutyl, tert-butyl, n-pentyl, isopentyl, neopentyl, and n-hexyl; linear or branched alkyloxys of 1 to 6 carbon atoms, such as methyloxy, ethyloxy, and propyloxy; alkenyls, such as vinyl and allyl; aryloxys, such as phenyloxy and tolyloxy; arylalkyloxys, such as benzyloxy and phenethyloxy; an aromatic hydrocarbon group or a condensed polycyclic aromatic group, such as phenyl, biphenylyl, terphenylyl, naphthyl, anthracenyl, phenanthrenyl, fluorenyl, indenyl, pyrenyl, perylenyl, fluoranthenyl, and triphenylenyl; an aromatic heterocyclic group, such as pyridyl, pyrimidinyl, triazinyl, furyl, thienyl, pyrrolyl, quinolyl, isoquinolyl, benzofuranyl, benzothienyl, indolyl, carbazolyl, benzoxazolyl, benzothiazolyl, quinoxalinyl, benzimidazolyl, pyrazolyl, dibenzofuranyl, dibenzothienyl, and carbolinyl; arylvinyls, such as styryl and naphthylvinyl; and acyls, such as acetyl and benzoyl. These substituents may be further substituted with the exemplified substituents above.

These substituents may bind to each other via a single bond, substituted or unsubstituted methylene, an oxygen atom, or a sulfur atom to form a ring.

Specific examples of the "aromatic heterocyclic group" in the "substituted or unsubstituted aromatic heterocyclic group" represented by B in the general formula (1) include pyridyl, bipyridyl, terpyridyl, pyrimidinyl, pyrazinyl, pyridazinyl, triazinyl, pyrrolyl, pyrazolyl, imidazolyl, triazolyl, oxazolyl, isoxazolyl, thiazolyl, isothiazolyl, oxadiazolyl, thiadiazolyl, furyl, thienyl, quinolyl, isoquinolyl, quinoxalinyl, quinazolinyl, naphthyridinyl, indolyl, isoindolyl, benzoimidazolyl, benzotriazolyl, benzofuranyl, benzothienyl, benzoxazolyl, benzoxadiazolyl, benzothiazolyl, benzothiadiazolyl, pyridopyrrolyl, pyridoimidazolyl, pyridotriazolyl, pteridinyl, acridinyl, phenazinyl, phenanthrolinyl, phenoxazinyl, phenothiazinyl, phenocelenazinyl, phenotellurazinyl, phenophosphinazinyl, carbazolyl, carbolinyl, dibenzofuranyl, dibenzothienyl, and xanthenyl.

Examples of the "substituent" in the "substituted aromatic heterocyclic group" represented by B in the general formula (1) include the same substituents exemplified as the "substituent" in the "substituted aromatic hydrocarbon" or the "substituted condensed polycyclic aromatics" in the "divalent group of a substituted aromatic hydrocarbon" or the "divalent group of a substituted condensed polycyclic aromatics" represented by $A^1$, $A^2$, and $A^3$ in the general formula (1), and possible embodiments may also be the same embodiments as the exemplified embodiments.

Specific examples of the "linear or branched alkyl of 1 to 20 carbon atoms", the "cycloalkyl of 5 to 10 carbon atoms", or the "linear or branched alkenyl of 2 to 20 carbon atoms" in the "linear or branched alkyl of 1 to 20 carbon atoms that may have a substituent", the "cycloalkyl of 5 to 10 carbon atoms that may have a substituent", or the "linear or branched alkenyl of 2 to 20 carbon atoms that may have a substituent" represented by $R^1$ to $R^{15}$ in the general formula (1) include methyl, ethyl, n-propyl, isopropyl, n-butyl, isobutyl, tert-butyl, n-pentyl, isopentyl, neopentyl, n-hexyl, n-heptyl, 2-methylhexyl, n-octyl, isooctyl, tert-octyl, 2-ethylhexyl, 3-methylheptyl, n-nonyl, n-decyl, n-hexadecyl, n-octadecyl, cyclopentyl, cyclohexyl, 1-adamantyl, 2-adamantyl, vinyl, allyl, isopropenyl, 2-butenyl, 1-pentenyl, 2-hexenyl, 1-heptenyl, 1-octenyl, 1-nonenyl, 1-decenyl, 1-undecenyl, 1-dodecenyl, 1-tridecenyl, 1-tetradecenyl, 1-pentadecenyl, 1-hexadecenyl, 1-heptadecenyl, 1-octadecenyl, 1-nonadecenyl, 1-eicocenyl, 2-heptenyl, 2-methyl-2-hexenyl, 2-octenyl, 2-ethylhexenyl, 3-methyl-2-heptenyl, 2-nonenyl, 2-decenyl, 2-hexadecenyl, and 2-octadecenyl. These groups may bind to each other via a single bond, substituted or unsubstituted methylene, an oxygen atom, or a sulfur atom to form a ring.

Specific examples of the "substituent" in the "linear or branched alkyl of 1 to 20 carbon atoms that has a substituent", the "cycloalkyl of 5 to 10 carbon atoms that has a substituent", or the "linear or branched alkenyl of 2 to 20 carbon atoms that has a substituent" represented by $R^1$ to $R^{15}$ in the general formula (1) include a deuterium atom, cyano, nitro; halogen atoms, such as a fluorine atom, a chlorine atom, a bromine atom, and an iodine atom; linear or branched alkyloxys of 1 to 6 carbon atoms, such as methyloxy, ethyloxy, and propyloxy; alkenyls, such as vinyl and allyl; aryloxys, such as phenyloxy and tolyloxy; arylalkyloxys, such as benzyloxy and phenethyloxy; and an aromatic hydrocarbon group or a condensed polycyclic aromatic group, such as phenyl, biphenylyl, terphenylyl, naphthyl, anthracenyl, phenanthrenyl, fluorenyl, indenyl, pyrenyl, perylenyl, fluoranthenyl, and triphenylenyl; an aromatic heterocyclic group, such as pyridyl, pyrimidinyl, triazinyl, thienyl, furyl, pyrrolyl, quinolyl, isoquinolyl, benzofuranyl, benzothienyl, indolyl, carbazolyl, benzoxazolyl, benzothiazolyl, quinoxalinyl, benzimidazolyl, pyrazolyl, dibenzofuranyl, dibenzothienyl, and carbolinyl. These substituents may be further substituted with the exemplified substituents above. These substituents may bind to each other via a single bond, substituted or unsubstituted methylene, an oxygen atom, or a sulfur atom to form a ring.

Specific examples of the "linear or branched alkyloxy of 1 to 20 carbon atoms" or the "cycloalkyloxy of 5 to 10 carbon atoms" in the "linear or branched alkyloxy of 1 to 20 carbon atoms that may have a substituent" or the "cycloalkyloxy of 5 to 10 carbon atoms that may have a substituent" represented by $R^1$ to $R^{15}$ in the general formula (1) include methyloxy, ethyloxy, n-propyloxy, isopropyloxy, n-butyloxy, tert-butyloxy, n-pentyloxy, n-hexyloxy, n-heptyloxy, 2-methylhexyloxy, n-octyloxy, isooctyloxy, tert-octyloxy, 2-ethylhexyloxy, 3-methylheptyloxy, n-nonyloxy, n-decyloxy, n-hexadecyloxy, n-octadecyloxy, cyclopentyloxy, cyclohexyloxy, cycloheptyloxy, cyclooctyloxy, 1-adamantyloxy, and 2-adamantyloxy. These groups may bind to each other via a single bond, substituted or unsubstituted methylene, an oxygen atom, or a sulfur atom to form a ring.

These groups may have a substituent. Examples of the substituent include the same groups exemplified as the "substituent" in the "linear or branched alkyl of 1 to 20 carbon atoms that has a substituent", the "cycloalkyl of 5 to 10 carbon atoms that has a substituent", or the "linear or branched alkenyl of 2 to 20 carbon atoms that has a substituent" represented by $R^1$ to $R^{15}$ in the general formula (1), and possible embodiments may also be the same embodiments as the exemplified embodiments.

Specific examples of the "aromatic hydrocarbon group", the "aromatic heterocyclic group", or the condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R^1$ to $R^{15}$ in the general formula (1) include phenyl, biphenylyl, terphenylyl, naphthyl, anthracenyl, phenanthrenyl, fluorenyl, indenyl, pyrenyl, perylenyl, fluoranthenyl, triphenylenyl, pyridyl, pyrimidinyl, triazinyl, furyl, pyrrolyl, thienyl, quinolyl, isoquinolyl, benzofuranyl, benzothienyl, indolyl, carbazolyl, benzoxazolyl, benzothiazolyl, quinoxalinyl, benzimidazolyl, pyrazolyl, dibenzofuranyl, dibenzothienyl, naphthyridinyl, phenanthrolinyl, acridinyl, and carbolinyl.

These groups may have a substituent. Examples of the substituent include the same groups exemplified as the "substituent" in the "substituted aromatic hydrocarbon" or the "substituted condensed polycyclic aromatics" in the "divalent group of a substituted aromatic hydrocarbon" or the "divalent group of a substituted condensed polycyclic aromatics" represented by $A^1$, $A^2$, and $A^3$ in the general formula (1), and possible embodiments may also be the same embodiments as the exemplified embodiments.

Specific examples of the "aryloxy group" in the "substituted or unsubstituted aryloxy group" represented by $R^1$ to $R^{15}$ in the general formula (1) include phenyloxy, biphenylyloxy, terphenylyloxy, naphthyloxy, anthracenyloxy, phenanthrenyloxy, fluorenyloxy, indenyloxy, pyrenyloxy, and perylenyloxy. These groups may bind to each other via a single bond, substituted or unsubstituted methylene, an oxygen atom, or a sulfur atom to form a ring.

These groups may have a substituent. Examples of the substituent include the same groups exemplified as the "substituent" in the "substituted aromatic hydrocarbon" or the "substituted condensed polycyclic aromatics" in the "divalent group of a substituted aromatic hydrocarbon" or the "divalent group of a substituted condensed polycyclic aromatics" represented by $A^1$, $A^2$, and $A^3$ in the general formula (1), and possible embodiments may also be the same embodiments as the exemplified embodiments.

Examples of the "aromatic hydrocarbon group", the "aromatic heterocyclic group", or the "condensed polycyclic aromatic group" in the "disubstituted amino group substituted with an aromatic hydrocarbon group, an aromatic heterocyclic group, or a condensed polycyclic aromatic group" represented by $R^1$ to $R^{15}$ in the general formula (1) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R^1$ to $R^{15}$ in the general formula (1).

These groups may have a substituent. Examples of the substituent include the same groups exemplified as the "substituent" in the "substituted aromatic hydrocarbon" or the "substituted condensed polycyclic aromatics" in the "divalent group of a substituted aromatic hydrocarbon" or the "divalent group of a substituted condensed polycyclic aromatics" represented by $A^1$, $A^2$, and $A^3$ in the general formula (1), and possible embodiments may also be the same embodiments as the exemplified embodiments.

In the "disubstituted amino group substituted with an aromatic hydrocarbon group, an aromatic heterocyclic group, or a condensed polycyclic aromatic group" represented by $R^1$ to $R^{15}$ in the general formula (1), these groups ($R^1$ to $R^{15}$) may bind to each other via a single bond, substituted or unsubstituted methylene, an oxygen atom, or a sulfur atom and via the "aromatic hydrocarbon group", the "aromatic heterocyclic group", or the "condensed polycyclic aromatic group" of these groups ($R^1$ to $R^{15}$) to form a ring.

$A^1$ in the general formula (1) is preferably a divalent group that results from the removal of two hydrogen atoms from benzene, biphenyl, naphthalene, fluorene, or phenanthrene, more preferably a divalent group that results from the removal of two hydrogen atoms from benzene or naphthalene, and particularly preferably a divalent group that results from the removal of two hydrogen atoms from benzene.

In the case where $A^1$ in the general formula (1) is a divalent group that results from the removal of two hydrogen atoms from benzene (phenylene), a preferred embodiment of the binding position of the phenylene as a binding group ($A^1$) for the two carbazole groups is preferably binding at the 1- and 3-positions of the benzene ring (m-phenylene) as shown by the following general formula (1a).

[Chemical Formula 5]

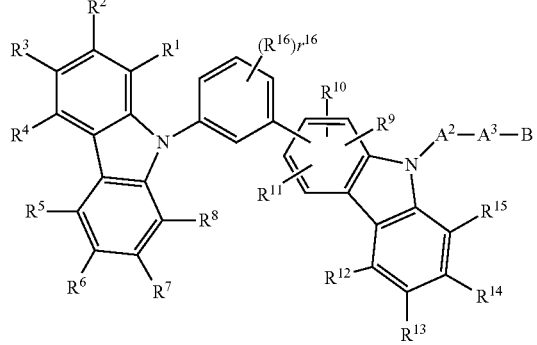

(1a)

In the formula, $R^{16}$ represents a substituent; $r^{16}$ represents an integer of 0 to 4; and $A^2$, $A^3$, B, and $R^1$ to $R^{15}$ have the same meanings as shown for the general formula (1).

$A^2$ in the general formula (1) is preferably a divalent group that results from the removal of two hydrogen atoms from benzene, biphenyl, naphthalene, fluorene, or phenanthrene, more preferably a divalent group that results from the removal of two hydrogen atoms from benzene or naphthalene, and particularly preferably a divalent group that results from the removal of two hydrogen atoms from benzene.

In the case where $A^2$ in the general formula (1) is a divalent group that results from the removal of two hydrogen atoms from benzene (phenylene), a preferred embodiment of the binding position of the phenylene as a binding group ($A^2$) is preferably binding at the 1- and 3-positions of the benzene ring (m-phenylene) as shown by the following general formula (1b-1) or at the 1- and 4-positions of the benzene ring (p-phenylene) as shown by the following general formula (1b-2), and more preferably binding at the 1- and 3-positions (m-phenylene).

[Chemical Formula 6]

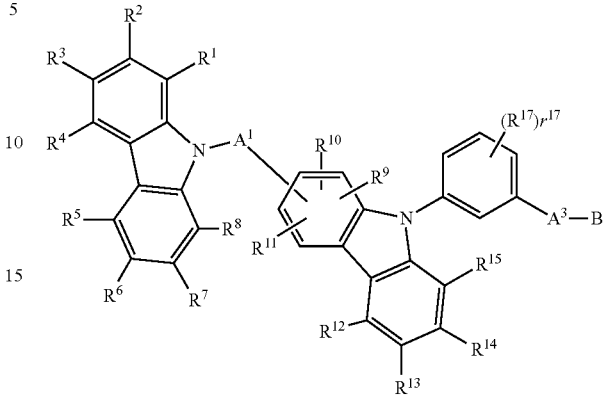

(1b-1)

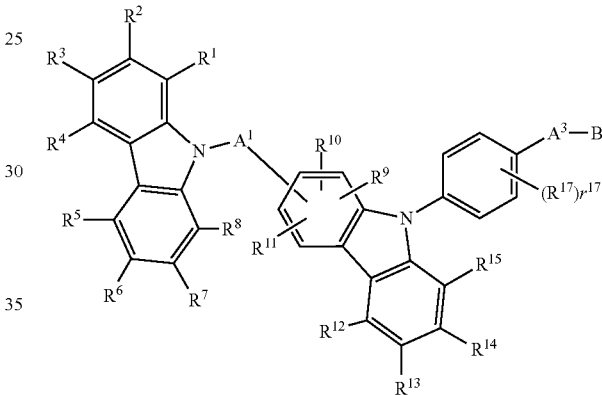

(1b-2)

In the formulae, $R^{17}$ represents a substituent; $r^{17}$ represents an integer of 0 to 4; and $A^1$, $A^3$, B, and $R^1$ to $R^{15}$ have the same meanings as shown for the general formula (1).

$A^3$ in the general formula (1) is preferably a divalent group that results from the removal of two hydrogen atoms from benzene, biphenyl, naphthalene, fluorene, or phenanthrene, or a single bond, more preferably a divalent group that results from the removal of two hydrogen atoms from benzene, biphenyl or naphthalene, or a single bond, and particularly preferably a divalent group that results from the removal of two hydrogen atoms from benzene or biphenyl, or a single bond.

In the case where $A^3$ in the general formula (1) is a divalent group that results from the removal of two hydrogen atoms from benzene (phenylene), a preferred embodiment of the binding position of the phenylene as a binding group ($A^3$) is preferably binding at the 1- and 3-positions of the benzene ring (m-phenylene) as shown by the following general formula (1c-1), or at the 1- and 4-positions of the benzene ring (p-phenylene) as shown by the following general formula (1c-2).

In the case where $A^3$ in the general formula (1) is a divalent group that results from the removal of two hydrogen atoms from biphenyl (biphenylene), 3,3'-biphenylene is preferred.

[Chemical Formula 7]

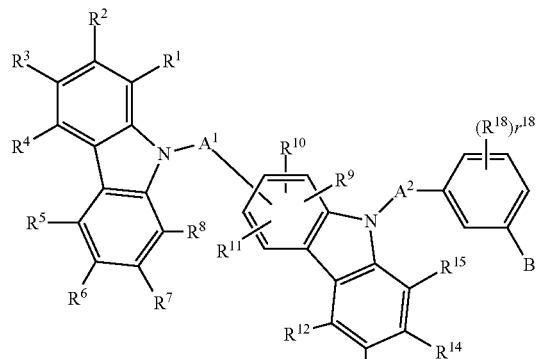

(1c-1)

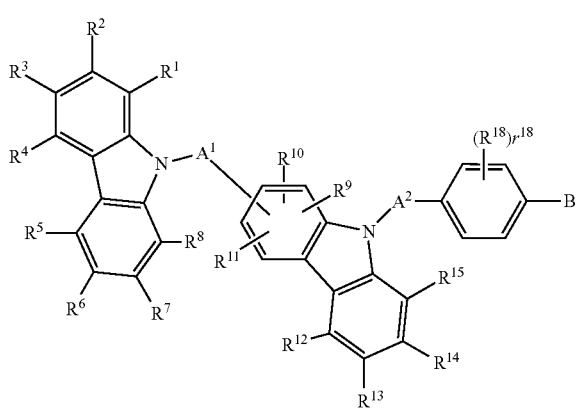

(1c-2)

In the formulae, $R^{18}$ represents a substituent; $r^{18}$ represents an integer of 0 to 4; and $A^1$, $A^2$, B, and $R^1$ to $R^{15}$ have the same meanings as shown for the general formula (1).

Examples of the "substituent" represented by $R^{16}$, $R^{17}$, and $R^{18}$ in the general formulae (1a), (1b-1), (1b-2), (1c-1), and (1c-2) include the same substituents exemplified as the "substituent" in the "substituted aromatic hydrocarbon" or the "substituted condensed polycyclic aromatics" in the "divalent group of a substituted aromatic hydrocarbon" or the "divalent group of a substituted condensed polycyclic aromatics" represented by $A^1$, $A^2$, and $A^3$ in the general formula (1). In the case where the plural substituents are present on the same benzene ring (i.e., the case where $r^{16}$, $r^{17}$, or $r^{18}$ is an integer of 2 to 4), these groups may bind to each other via a single bond, substituted or unsubstituted methylene, an oxygen atom, or a sulfur atom to form a ring.

These groups may be substituted with a substituent exemplified as the "substituent" in the "substituted aromatic hydrocarbon" or the "substituted condensed polycyclic aromatics" in the "divalent group of a substituted aromatic hydrocarbon" or the "divalent group of a substituted condensed polycyclic aromatics" represented by $A^1$, $A^2$, and $A^3$ in the general formula (1), and these substituents may bind to each other via a single bond, substituted or unsubstituted methylene, an oxygen atom, or a sulfur atom to form a ring.

The "substituted or unsubstituted aromatic heterocyclic group" represented by B in the general formula (1) is preferably a nitrogen-containing heterocyclic group that has high electron acceptability, such as pyridyl, bipyridyl, terpyridyl, pyrimidinyl, pyrazinyl, pyridazinyl, triazinyl, pyrazolyl, imidazolyl, triazolyl, oxazolyl, isoxazolyl, thiazolyl, isothiazolyl, oxadiazolyl, thiadiazolyl, quinolyl, isoquinolyl, quinoxalinyl, quinazolinyl, naphthyridinyl, indolyl, isoindolyl, benzimidazolyl, benzotriazolyl, benzoxazolyl, benzoxadiazolyl, benzothiazolyl, benzothiadiazolyl, pyridopyrrolyl, pyridoimidazolyl, pyridotriazolyl, pteridinyl, acridinyl, phenazinyl, phenanthrolinyl, carbolinyl, and xanthenyl, or a group that has these groups as a partial structure thereof, more preferably pyridyl, bipyridyl, terpyridyl, pyrimidinyl, pyrazinyl, triazinyl, quinolyl, isoquinolyl, quinoxalinyl, quinazolinyl, naphthyridinyl, benzimidazolyl, benzotriazolyl, benzothiadiazolyl, pyridopyrrolyl, pyridoimidazolyl, pyridotriazolyl, phenanthrolinyl, or carbolinyl, and particularly preferably a monocyclic (not forming a condensed ring) nitrogen-containing heterocyclic group, such as pyridyl, pyrimidinyl, pyrazinyl, and triazinyl, since a favorable excitation triplet level is provided.

In the compound having a carbazole ring structure represented by the general formula (1), one of the binding positions of the two carbazole rings is the 9-position (nitrogen atom), and the other one of the positions may be any of the 1- to 4-positions, and is preferably the 1-position as shown by the following general formula (1d-1) or the 2-position as shown by the following general formula (1d-2).

[Chemical Formula 8]

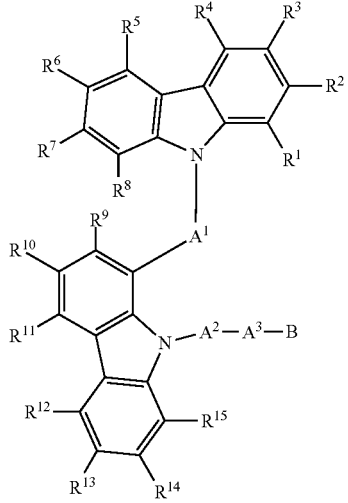

(1d-1)

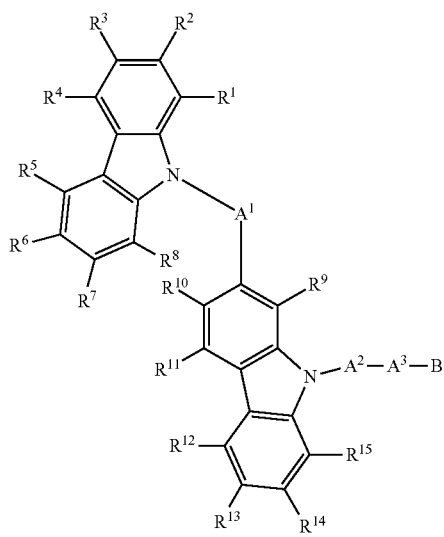

(1d-2)

In the formula, $A^1$, $A^2$, $A^3$, B, $R^1$ to $R^{15}$ are as defined in the general formula (1).

The "linear or branched alkyl of 1 to 20 carbon atoms" in the "linear or branched alkyl of 1 to 20 carbon atoms that may have a substituent" represented by $R^1$ to $R^{15}$ in the general formula (1) is preferably the "linear or branched alkyl of 1 to 6 carbon atoms", such as methyl, ethyl, n-propyl, isopropyl, n-butyl, isobutyl, tert-butyl, n-pentyl, isopentyl, neopentyl, and n-hexyl.

The "linear or branched alkenyl of 2 to 20 carbon atoms" in the "linear or branched alkenyl of 2 to 20 carbon atoms that may have a substituent" represented by $R^1$ to $R^{15}$ in the general formula (1) is preferably the "linear or branched alkenyl of 2 to 6 carbon atoms", such as vinyl, allyl, isopropenyl, and 2-butenyl.

The "linear or branched alkyloxy of 1 to 20 carbon atoms" in the "linear or branched alkyloxy of 1 to 20 carbon atoms that may have a substituent" represented by $R^1$ to $R^{15}$ in the general formula (1) is preferably the "linear or branched alkyloxy of 1 to 6 carbon atoms", such as methyloxy, ethyloxy, n-propyloxy, isopropyloxy, n-butyloxy, tert-butyloxy, n-pentyloxy, and n-hexyloxy.

The light-emitting material containing the compound having a carbazole ring structure represented by the general formula (1) of the invention has a favorable excitation triplet level as a light-emitting material (host material) of a light emitting layer that emits phosphorescence or a light emitting layer that emits delayed fluorescence, and has an excellent capability as a light-emitting material (host material) of a light emitting layer, and particularly as a light-emitting material (host material) of a light emitting layer that emits delayed fluorescence.

The light-emitting material containing the compound having a carbazole ring structure represented by the general formula (1) of the invention can be used as a constitutional material of a light emitting layer of an organic EL device. The use of the light-emitting material containing the compound of the invention, which is excellent in bipolar transporting property compared to the ordinary materials, provides such effects as the enhancement of the power efficiency and the decrease of the practical operation voltage.

Advantageous Effects of Invention

The light-emitting material containing the compound having a carbazole ring structure represented by the general formula (1) of the invention is useful as a host material of a light emitting layer of an organic EL device, and the production of an organic EL device by using the material can provide an organic EL device that has a high luminous efficiency and a low operation voltage.

DESCRIPTION OF EMBODIMENTS

Figure 1:
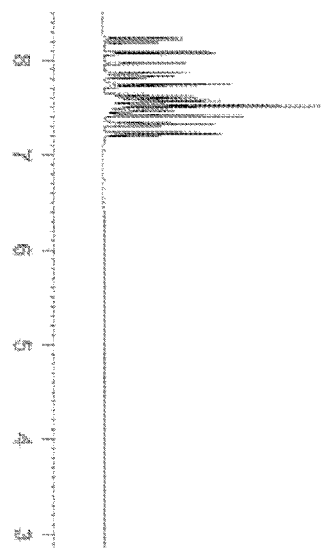
FIG. 1 is a $^1$H-NMR chart of the compound (compound 6) of Example 1 of the present invention.

The compound having a carbazole ring structure represented by the general formula (1) can be synthesized, for example, in the following manner. A compound having two carbazole rings binding via a divalent group of an aromatic hydrocarbon or via a divalent group of a condensed polycyclic aromatics can be synthesized by performing cross-coupling reaction, such as Suzuki coupling reaction, of a carbazole derivative having a halogenated aryl introduced to the 9-position thereof and a boronic acid or a boronate ester of a carbazole derivative, or condensation reaction, such as Buchwald-Hartwig reaction, of a carbazole derivative having a halogen group, such as a bromo group, or a trifluoromethanesulfonyloxy group introduced thereto and a carbazole derivative.

The compound having a carbazole ring structure represented by the general formula (1) can be synthesized by performing condensation reaction, such as Buchwald-Hartwig reaction, of the compound having two carbazole rings binding via a divalent group of an aromatic hydrocarbon or via a divalent group of a condensed polycyclic aromatics and a halogenated aryl having an aromatic heterocyclic group as a substituent.

In alternative, the compound having a carbazole ring structure represented by the general formula (1) can also be synthesized by introducing a halogenated aryl to the compound having two carbazole rings binding via a divalent group of an aromatic hydrocarbon or via a divalent group of a condensed polycyclic aromatics in advance to form a boronic acid or a boronate ester, and subsequently performing cross-coupling reaction, such as Suzuki coupling reaction, with a halogenated aryl having an aromatic heterocyclic group as a substituent.

The following presents specific examples of preferred compounds among the compounds of the general formula (1) having a carbazole ring structure. The present invention, however, is not restricted to these compounds.

[Chemical Formula 9]

(Compound 1)

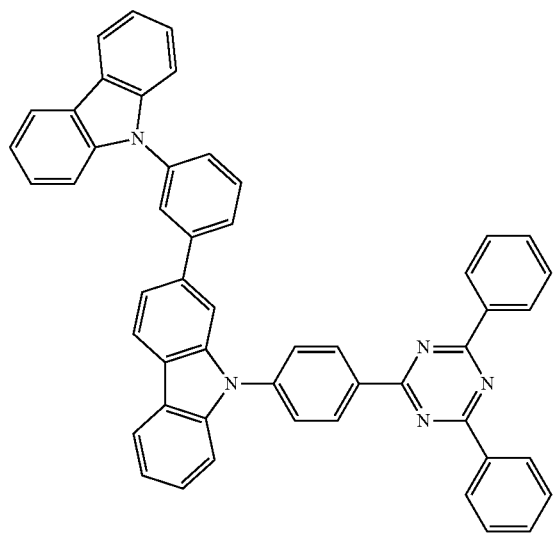

[Chemical Formula 10]
(Compound 2)
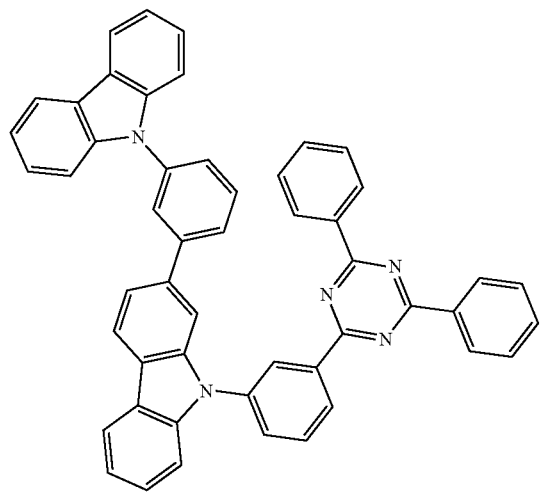
[Chemical Formula 11]
(Compound 3)
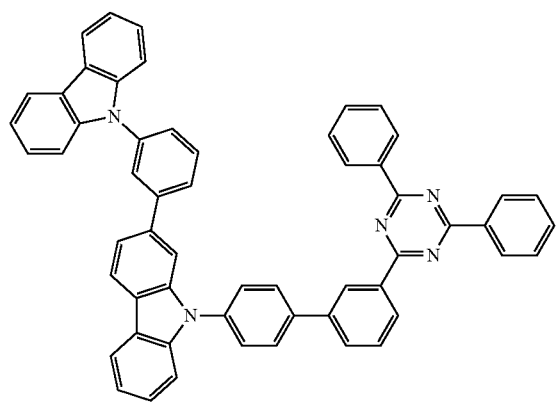
[Chemical Formula 12]
(Compound 4)
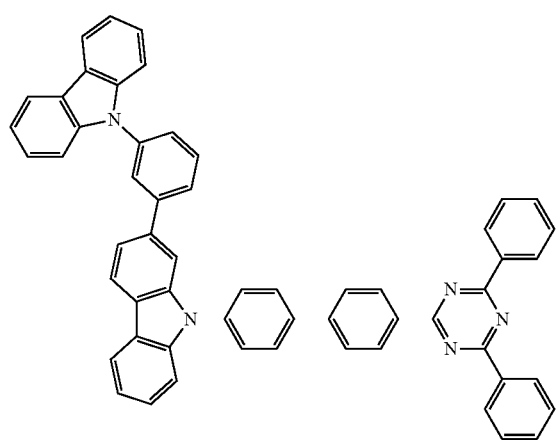
[Chemical Formula 13]
(Compound 5)
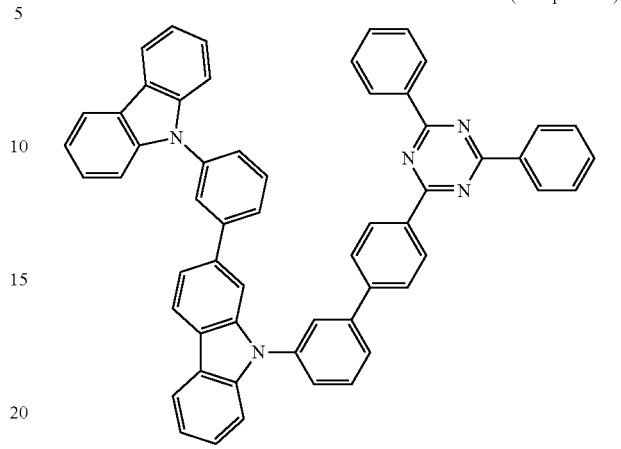
[Chemical Formula 14]
(Compound 6)
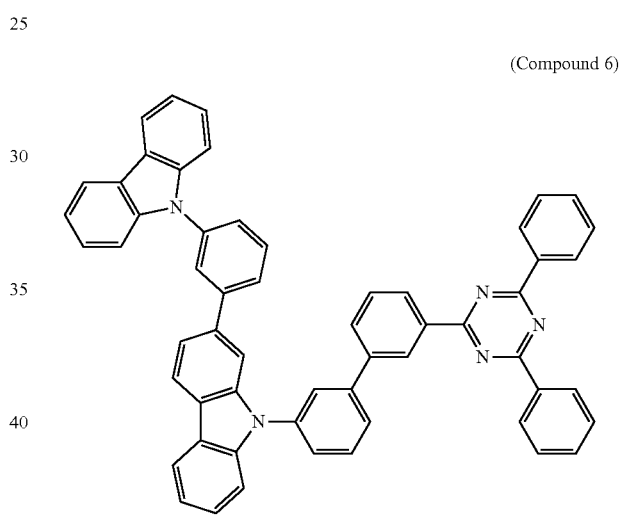
[Chemical Formula 15]
(Compound 7)
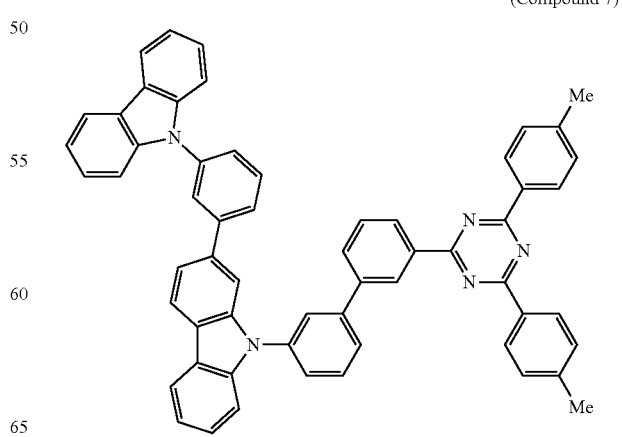

[Chemical Formula 16]
(Compound 8)
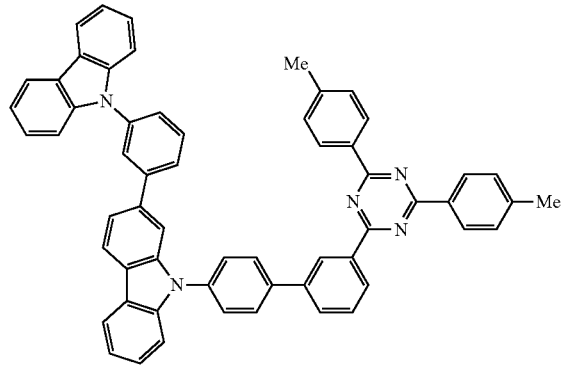
[Chemical Formula 17]
(Compound 9)
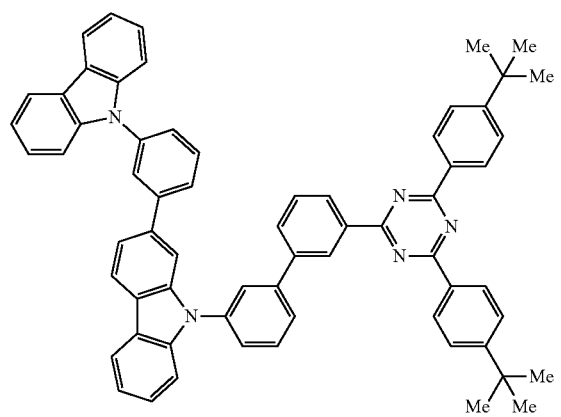
[Chemical Formula 18]
(Compound 10)
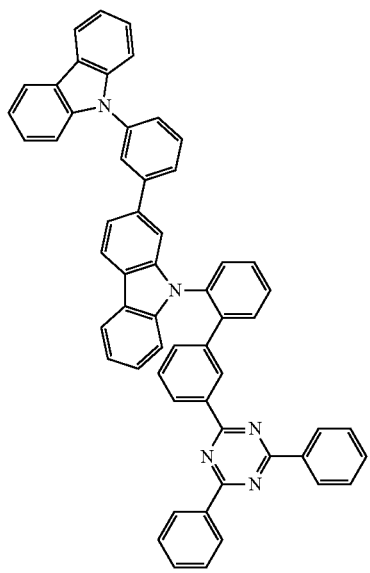
[Chemical Formula 19]
(Compound 11)
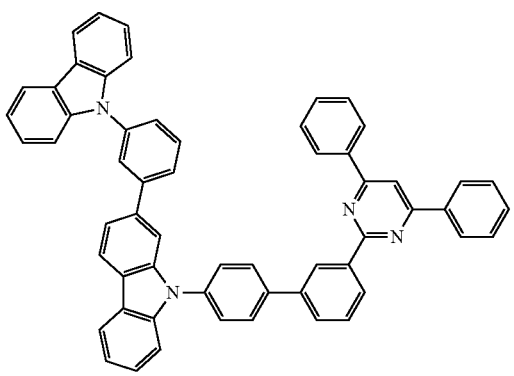
[Chemical Formula 20]
(Compound 12)
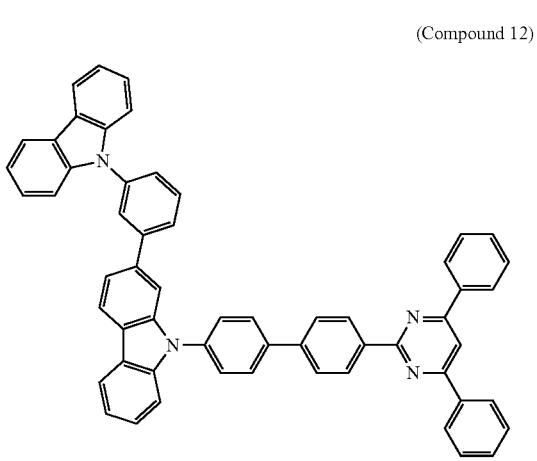
[Chemical Formula 21]
(Compound 13)
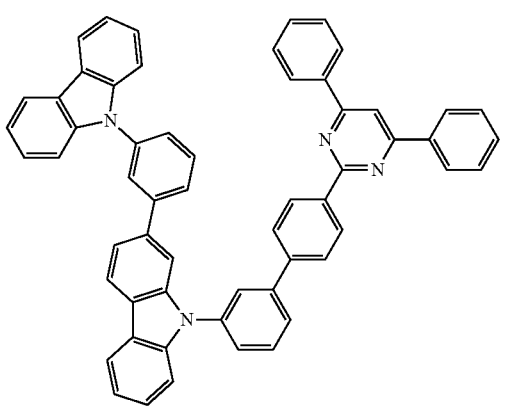

[Chemical Formula 22]
(Compound 14)
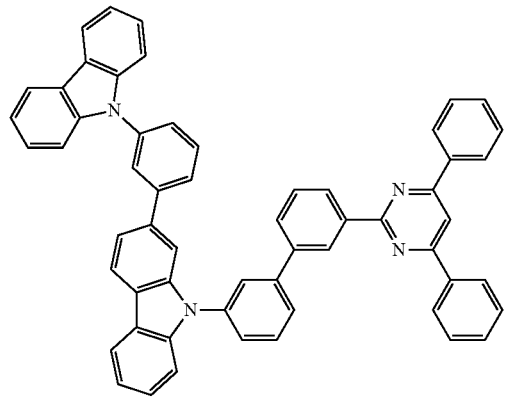
[Chemical Formula 23]
(Compound 15)
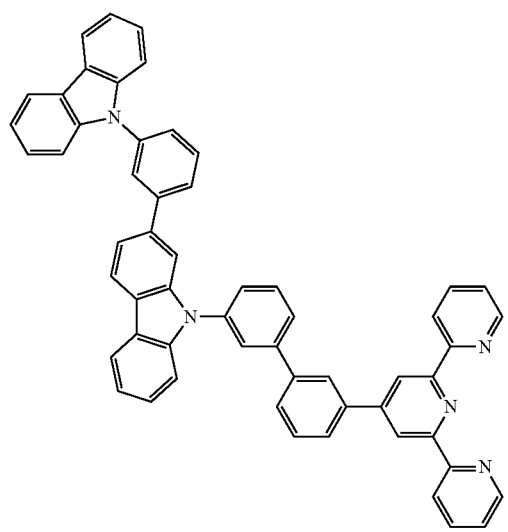
[Chemical Formula 24]
(Compound 16)
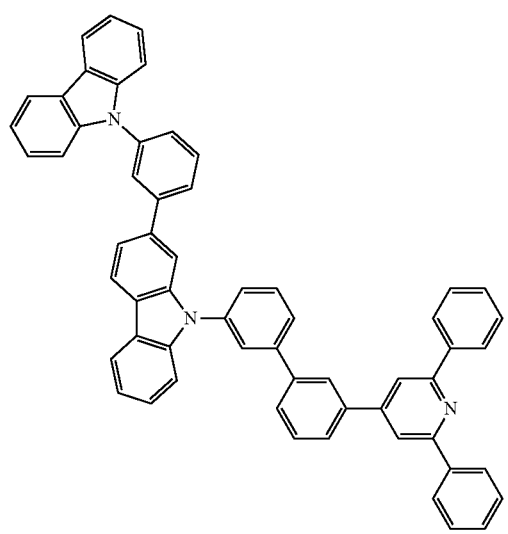
[Chemical Formula 25]
(Compound 17)
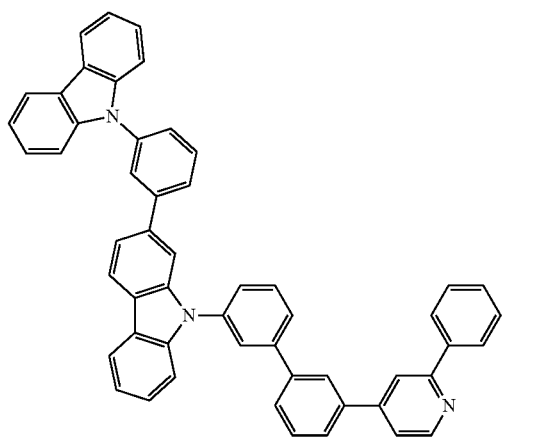
[Chemical Formula 26]
(Compound 18)
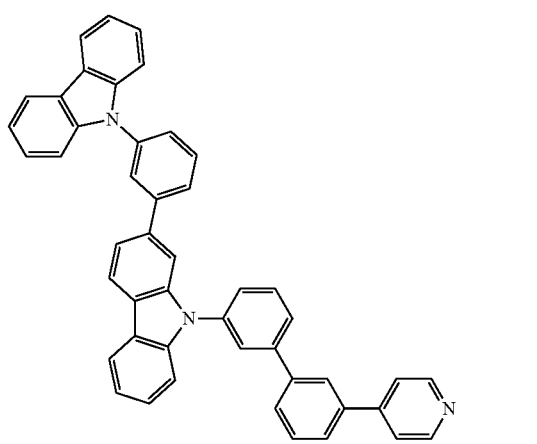
[Chemical Formula 27]
(Compound 19)
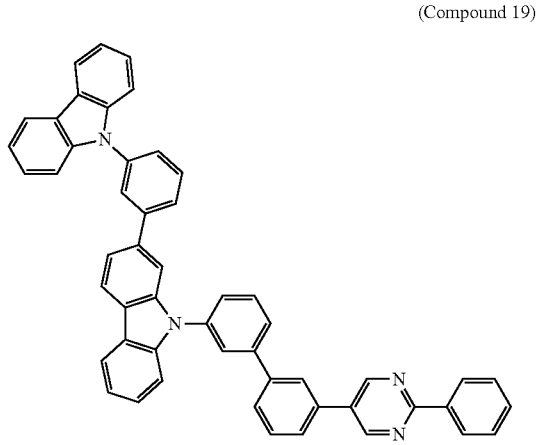

[Chemical Formula 28]
(Compound 20)
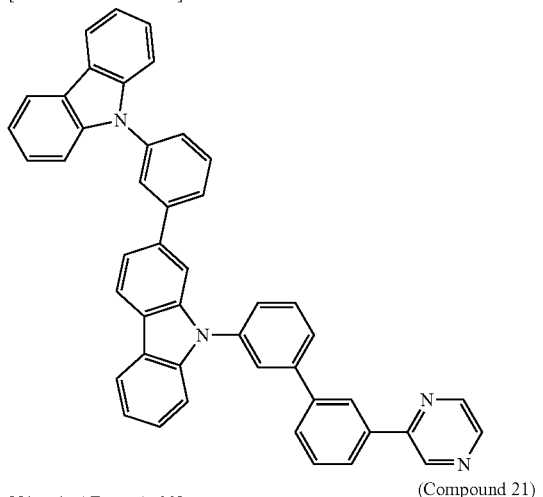
[Chemical Formula 29]
(Compound 21)
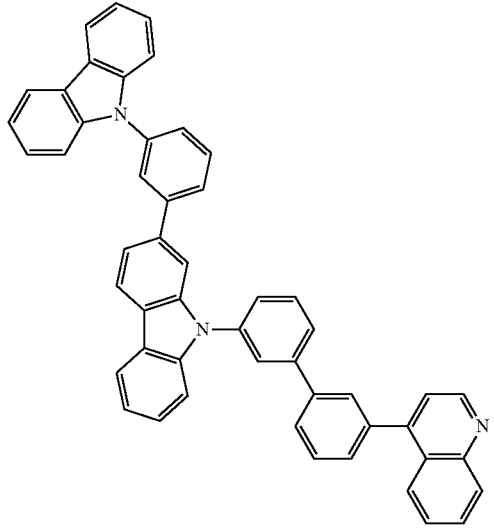
[Chemical Formula 30]
(Compound 22)
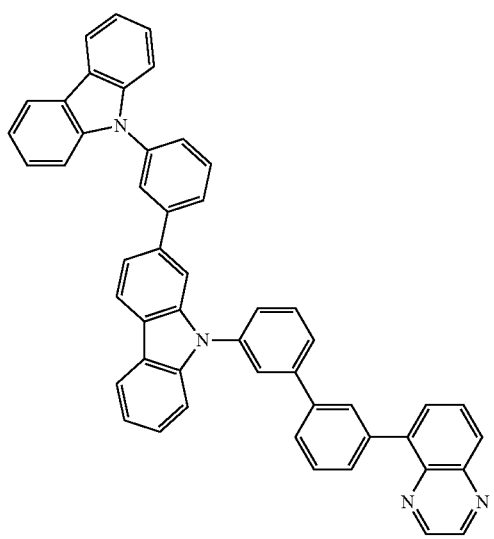
[Chemical Formula 31]
(Compound 23)
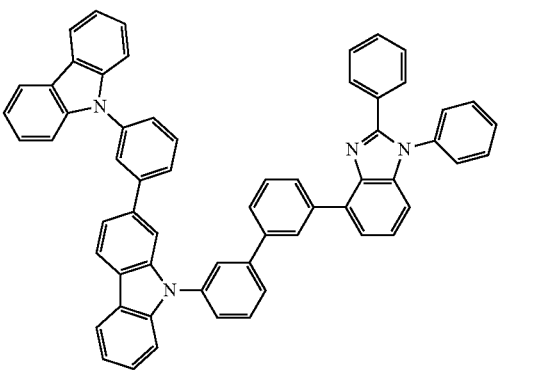
[Chemical Formula 32]
(Compound 24)
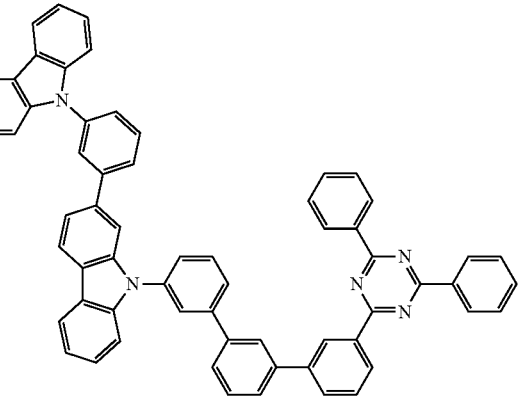
[Chemical Formula 33]
(Compound 25)
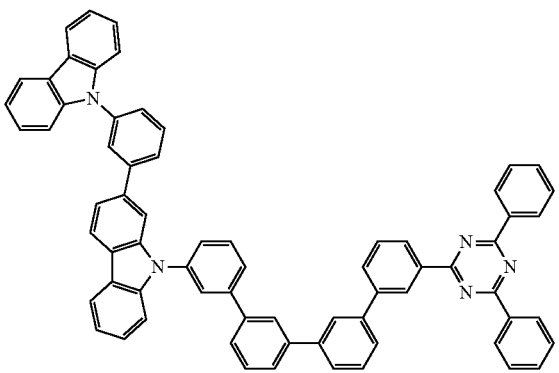

[Chemical Formula 34]
(Compound 26)
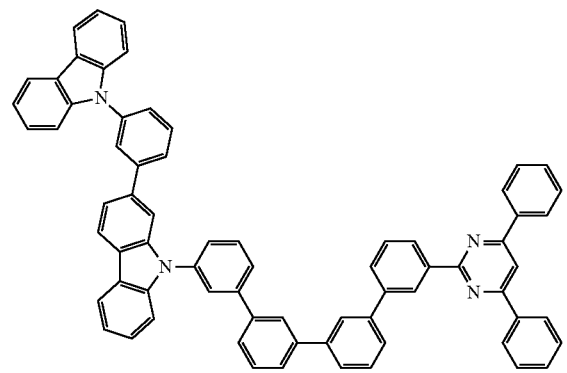
[Chemical Formula 35]
(Compound 27)
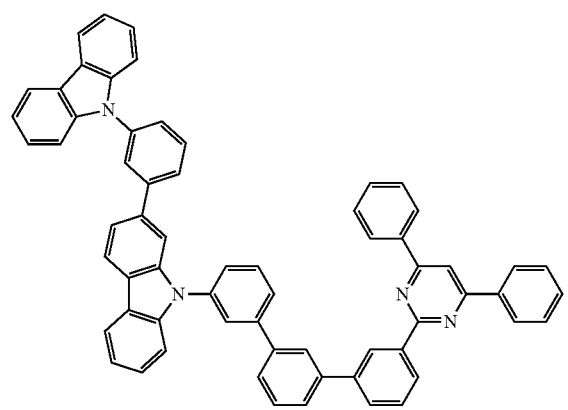
[Chemical Formula 36]
(Compound 28)
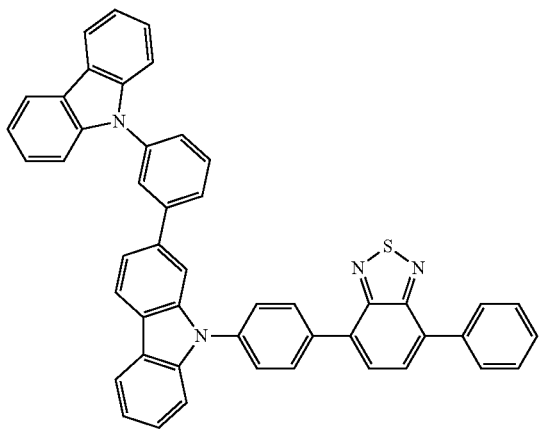
[Chemical Formula 37]
(Compound 29)
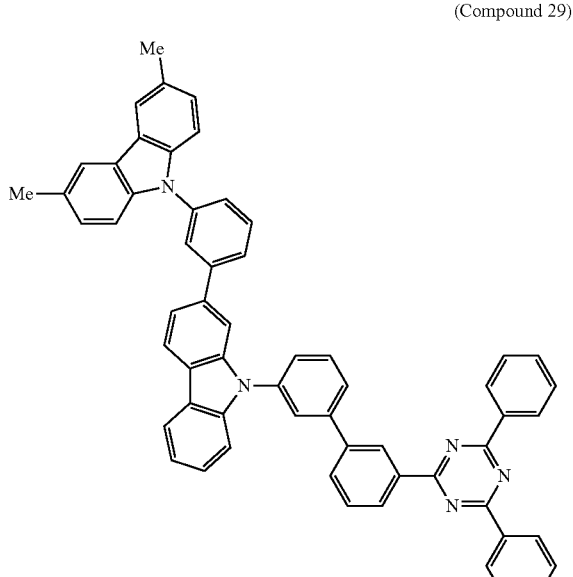
[Chemical Formula 38]
(Compound 30)
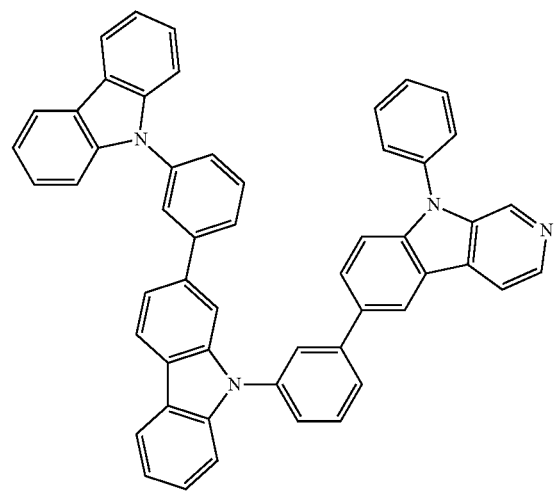

-continued
[Chemical Formula 39]
(Compound 31)
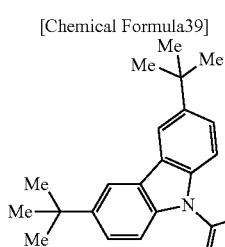
[Chemical Formula 40]
(Compound 32)
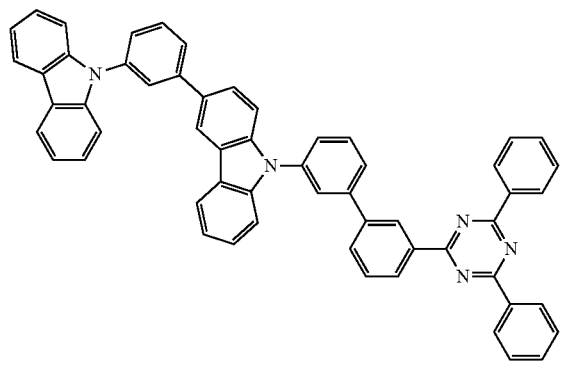
[Chemical Formula 41]
(Compound 33)
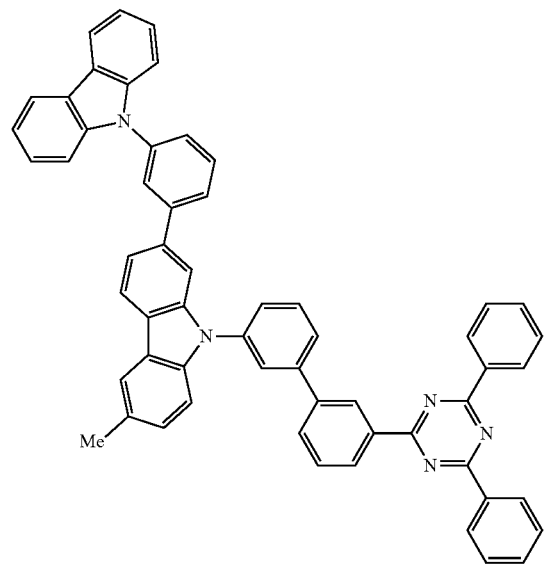
-continued
[Chemical Formula 42]
(Compound 34)
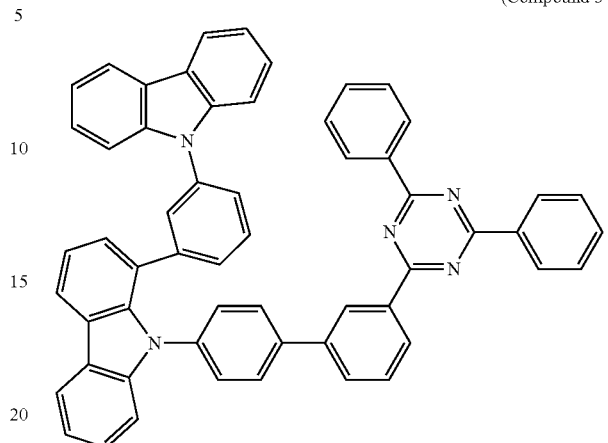
[Chemical Formula 43]
(Compound 35)
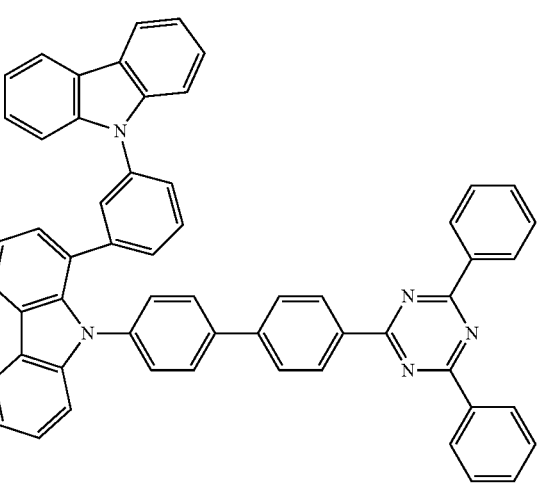
[Chemical Formula 44]
(Compound 36)
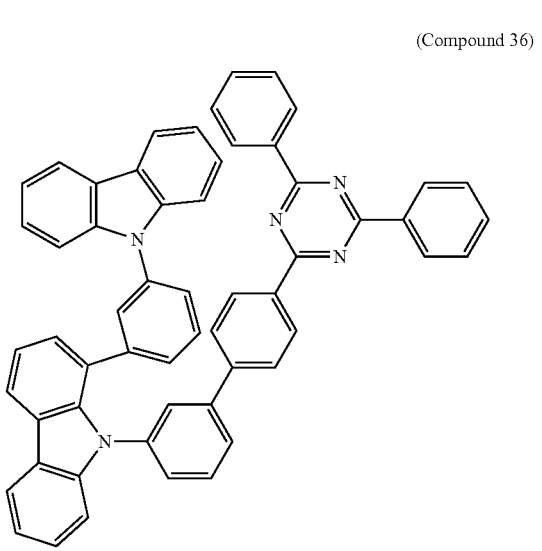

[Chemical Formula 45]

(Compound 37)

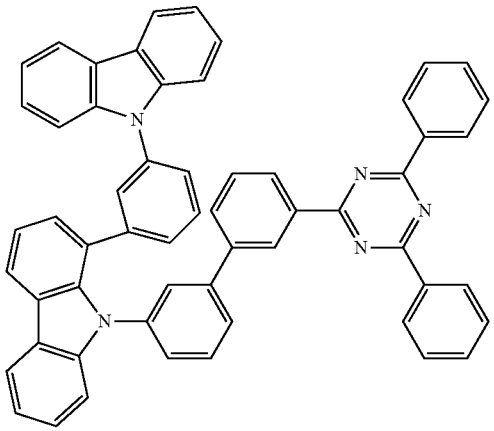

[Chemical Formula 46]

(Compound 38)

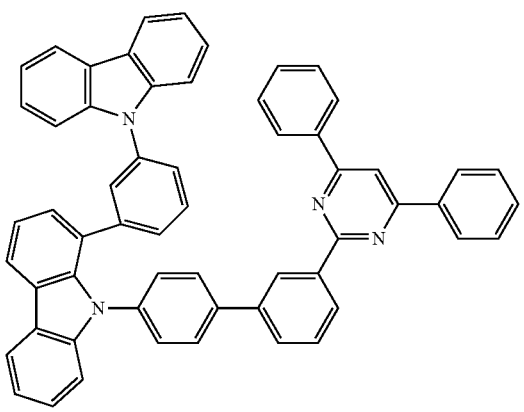

[Chemical Formula 47]

(Compound 39)

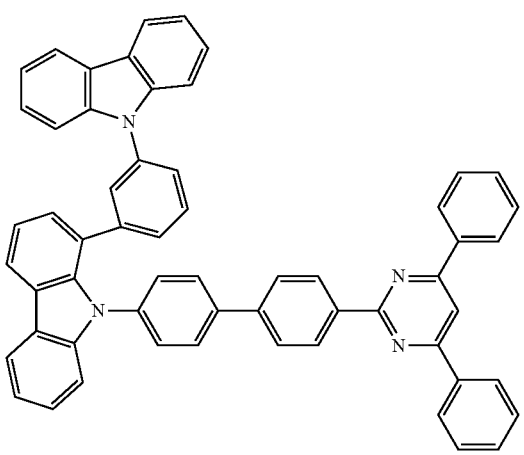

[Chemical Formula 48]

(Compound 40)

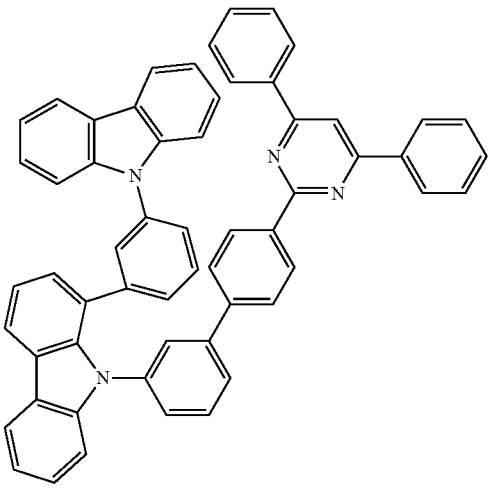

[Chemical Formula 49]

(Compound 41)

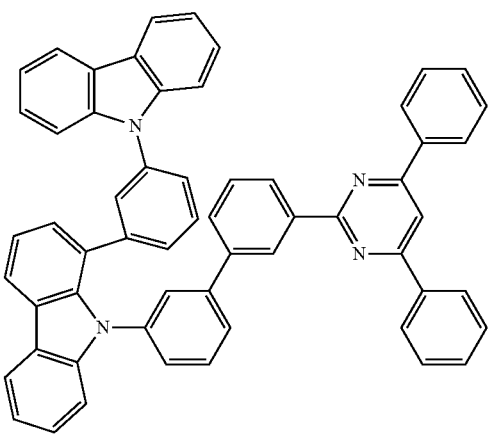

These compounds were purified by methods such as column chromatography, adsorption using, for example, a silica gel, activated carbon, or activated clay, recrystallization or crystallization using a solvent, and a sublimation purification method. The compounds were identified by an NMR analysis.

As a property value thereof, a work function thereof was measured. The work function is an index of the energy level as a material of a light emitting layer or an index of a hole blocking capability.

For the measurement of work function, a 100 nm-thick thin film was fabricated on an ITO substrate, and an atmosphere photoelectron spectrometer (AC-3 produced by Riken Keiki Co., Ltd.) was used.

Examples of the structure of the organic EL device of the present invention include a structure containing an anode, a hole transport layer, a light emitting layer, an electron transport layer, an electron injection layer, and a cathode successively formed on a substrate, optionally with a hole injection layer between the anode and the hole transport layer, an electron blocking layer between the light emitting layer and the hole transport layer, a hole blocking layer between the light emitting layer and the electron transport layer, and an exciton blocking layer on the anode side and/or the cathode side of the light emitting layer. Some of the organic layers in the multilayer structure may be omitted, for example, a single organic layer may serve as the electron injection layer and the electron transport layer, i.e., a structure containing an anode, a hole transport layer, a light emitting layer, an electron transport layer, and a cathode successively formed on a substrate.

Furthermore, two or more organic layers having the same function may be laminated, for example, two layers of the hole transport layers may be laminated, two layers of the light emitting layers may be laminated, and two layers of the electron transport layers may be laminated.

An electrode material having a high work function, such as ITO and gold, may be used as the anode of the organic EL device of the present invention. The hole injection layer used of the organic EL device of the present invention may be a porphyrin compound, represented by copper phthalocyanine, and also may be a naphthalenediamine derivative, a starburst type triphenylamine derivative, a triphenylamine trimer or tetramer, such as an arylamine compound having a structure containing in the molecule thereof three or more triphenylamine structures binding via a single bond or a divalent group containing no hetero atom, a heterocyclic compound having acceptor property, such as hexacyanoazatriphenylene, or a coating type polymer compound. These materials may be formed into a thin film by a vapor deposition method or other known methods such as a spin coating method and an inkjet method.

The hole transport layer used of the organic EL device of the present invention may be a compound containing a m-carbazolylphenyl group, and also may be a benzidine derivative, such as N,N'-diphenyl-N,N'-di(m-tolyl)-benzidine (TPD), N,N'-diphenyl-N,N'-di(a-naphthyl)-benzidine (NPD), and N,N,N',N'-tetrabiphenylylbenzidine, 1,1-bis[(di-4-tolylamino)phenyl]cyclohexane (TAPC), and various triphenylamine trimers and tetramers. These compounds each may be individually formed into a film, may be used as a single layer formed with another material mixed, or may be formed into a laminated structure containing the individually formed layers, a laminated structure containing the layers with another material mixed, or a laminated structure containing the individually formed layer and the layer with another material mixed. The hole injection or transport layer used may be a coating type polymer material, such as poly(3,4-ethylenedioxythiophene) (PEDOT)/poly(styrenesulfonate) (PSS). These materials may be formed into a thin film by a vapor deposition method or other known methods such as a spin coating method and an inkjet method.

In the hole injection layer or the hole transport layer, a material that is ordinarily used in the layer p-doped with trisbromophenylamine hexachloro antimony, a radialene derivative (see, for example, WO 2014/009310), or the like, a polymer compound having a structure of a benzidine derivative, such as TPD, as a partial structure thereof, or the like may be used.

The electron blocking layer used of the organic EL device of the present invention may be a compound having an electron blocking capability, such as a carbazole derivative, such as 4,4',4''-tri(N-carbazolyl)triphenylamine (TCTA), 9,9-bis[4-(carbazol-9-yl)phenyl]fluorene, 1,3-bis(carbazol-9-yl)benzene (mCP), and 2,2-bis(4-carbazol-9-ylphenyl) adamantane (Ad-Cz), a compound having a triphenylsilyl group and a triarylamine structure, represented by 9-[4-(carbazol-9-yl)phenyl]-9-[4-(triphenylsilyl)phenyl]-9H-fluorene, a monoamine compound having high electron blocking property, and various triphenylamine dimers. These compounds each may be individually formed into a film, may be used as a single layer formed with another material mixed, or may be formed into a laminated structure containing the individually formed layers, a laminated structure containing the layers with another material mixed, or a laminated structure containing the individually formed layer and the layer with another material mixed. These materials may be formed into a thin film by a vapor deposition method or other known methods such as a spin coating method and an inkjet method.

The light emitting layer used of the organic EL device of the present invention is preferably the light-emitting material containing the compound having a carbazole ring structure represented by the general formula (1). In addition, various metal complexes, such as a metal complex of a quinolinol derivative, e.g., $Alq_3$, a compound having a pyrimidine ring structure, an anthracene derivative, a bis-stylylbenzene derivative, a pyrene derivative, an oxazole derivative, a poly-p-phenylenevinylene derivative, and the like can be used. The light emitting layer may be formed of a host material and a dopant material, and in this case, the host material used is preferably the light-emitting material containing the compound having a carbazole ring structure represented by the general formula (1), and in addition, mCP, a thiazole derivative, a benzimidazole derivative, a polydialkylfluorene derivative, a heterocyclic compound having an indole ring as a partial structure of a condensed ring, and the like can be used. The dopant material used may be a pyrene derivative, an anthracene derivative, quinacridone, coumarin, rubrene, perylene, and derivatives thereof, a benzopyran derivative, a rhodamine derivative, an aminostyryl derivative, a spirobifluorene derivative, and the like. These compounds each may be individually formed into a film, may be used as a single layer formed with another material mixed, or may be formed into a laminated structure containing the individually formed layers, a laminated structure containing the layers with another material mixed, or a laminated structure containing the individually formed layer and the layer with another material mixed.

In the light emitting layer of the organic EL device of the present invention, a phosphorescent light-emitting material as a light-emitting material is preferably used as a dopant material. The phosphorescent light-emitting material used may be a phosphorescent light-emitting material of a metal complex of iridium, platinum, or the like. A green phosphorescent light-emitting material, such as $Ir(ppy)_3$, a blue phosphorescent light-emitting material, such as FIrpic and FIr6, a red phosphorescent light-emitting material, such as $Btp_2Ir(acac)$, may be used, and the host material used therefor is preferably the light-emitting material containing the compound having a carbazole ring structure represented by the general formula (1), and in addition, a heterocyclic compound having an indole ring as a partial structure of a condensed ring, and as a hole injection/transport host material, a carbazole derivative, such as 4,4'-di(N-carbazolyl) biphenyl (CBP), TCTA, and mCP, may be used. The electron transport host material used may be p-bis(triphenylsilyl) benzene (UGH2), 2,2',2''-(1,3,5-phenylene)-tris(1-phenyl-1H-benzimidazole) (TPBI), and the like, and thereby an organic EL device having high performance can be produced.

In order to avoid concentration quenching, the doping of the host material with the phosphorescent light-emitting material is preferably made by co-evaporation in a range of 1 to 30% by weight with respect to the total light emitting layer.

In the light emitting layer of the organic EL device of the present invention, a material emitting delayed fluorescence as a light-emitting material is more preferably used as a dopant material. The material emitting delayed fluorescence used may be a CDCB derivative, such as PIC-TRZ, CC2TA, PXZ-TRZ, and 4CzIPN, and the like (see, for example, NPLs 3 and 8), and the host material used therefor is preferably the light-emitting material containing the compound having a carbazole ring structure represented by the general formula (1), and in addition, the aforementioned dopant materials preferred for the case using the phosphorescent light-emitting material may be used, such as a carbazole derivative, such as CBP, TCTA, and mCP, and a heterocyclic compound having an indole ring as a partial structure of a condensed ring.

In this case, an embodiment using a mixture of the material emitting delayed fluorescence and the light-emitting materials described above, particularly the fluorescent light-emitting material (dopant material), is also preferred, and an embodiment using a mixture of the light-emitting material containing the compound having a carbazole ring structure represented by the general formula (1) and the aforementioned light-emitting material (host material) is also preferred.

These materials may be formed into a thin film by a vapor deposition method or other known methods such as a spin coating method and an inkjet method.

A device may be produced to have a structure containing a light emitting layer produced by using the light-emitting material containing the compound having a carbazole ring structure represented by the general formula (1) having laminated adjacently thereon a light emitting layer produced by using a compound having a different work function as a host material (see, for example, NPL 9).

The hole blocking layer used of the organic EL device of the present invention may be the compound having a carbazole ring structure represented by the general formula (1), and also may be a phenanthroline derivative, e.g., bathocuproine (BCP), a metal complex of a quinolinol derivative, such as aluminum(III) bis(2-methyl-8-quinolinato)-4-phenylphenolate (BAlq), and hole blocking compounds, such as various kinds of a rare earth derivative, an oxazole derivative, a triazole derivative, and a triazine derivative. These materials may also serve as the material of the electron transport layer. These compounds each may be individually formed into a film, may be used as a single layer formed with another material mixed, or may be formed into a laminated structure containing the individually formed layers, a laminated structure containing the layers with another material mixed, or a laminated structure containing the individually formed layer and the layer with another material mixed. These materials may be formed into a thin film by a vapor deposition method or other known methods such as a spin coating method and an inkjet method.

The electron transport layer used of the organic EL device of the present invention may be a metal complex of a quinolinol derivative, such as $Alq_3$ and BAlq, and may be various kinds of a metal complex, a triazole derivative, a triazine derivative, an oxadiazole derivative, a pyridine derivative, a benzimidazole derivative, a thiadiazole derivative, an anthracene derivative, a carbodiimide derivative, a quinoxaline derivative, a pyridoindole derivative, a phenanthroline derivative, and a silole derivative. These compounds each may be individually formed into a film, may be used as a single layer formed with another material mixed, or may be formed into a laminated structure containing the individually formed layers, a laminated structure containing the layers with another material mixed, or a laminated structure containing the individually formed layer and the layer with another material mixed. These materials may be formed into a thin film by a vapor deposition method or other known methods such as a spin coating method and an inkjet method.

The electron injection layer used of the organic EL device of the present invention may be an alkali metal salt, such as lithium fluoride and cesium fluoride, an alkaline earth metal salt, such as magnesium fluoride, a metal complex of a quinolinol derivative, such as lithium quinolinol, a metal oxide, such as aluminum oxide, and the like, and may be omitted in the preferred selection of the electron transport layer and the cathode.

In the electron injection layer or the electron transport layer, a material that is ordinarily used in the layers having been n-doped with a metal, such as cesium, a triarylphosphine oxide derivative (see, for example, WO 2014/195482), or the like may also be used.

The electrode material of the cathode used of the organic EL device of the present invention may be an electrode material having a low work function, such as aluminum, or an alloy having a lower work function, such as a magnesium-silver alloy, a magnesium-indium alloy, or an aluminum-magnesium alloy.

Preferred materials that can be used in the organic EL device of the present invention will be specifically shown below. However, the materials that can be used in the present invention are not construed as being limited to the following example compounds. A compound that is exemplified as a material having a particular function may be applied to a material having another function. In the following structural formulae of the example compounds, R and $R_2$ to $R_7$ each independently represents a hydrogen atom or a substituent, and n represents an integer of 3 to 5.

Preferred examples of a compound that may also be used as the host material of the light emitting layer are shown below.

[Chemical Formula 50]

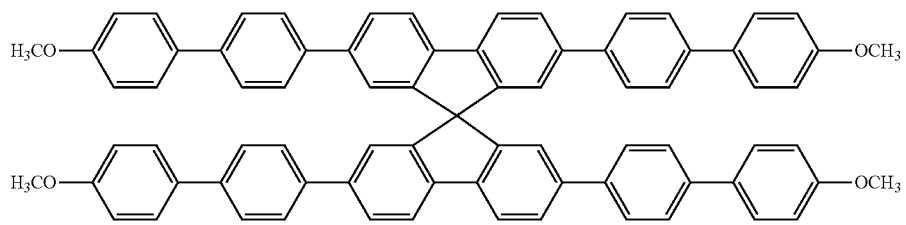

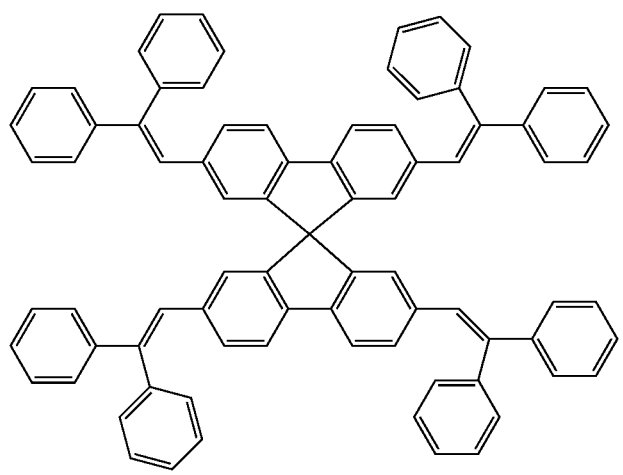
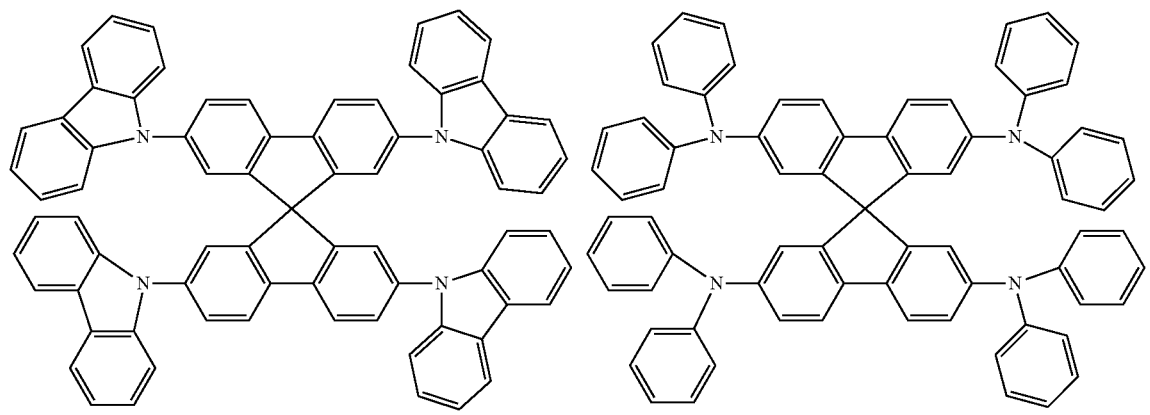
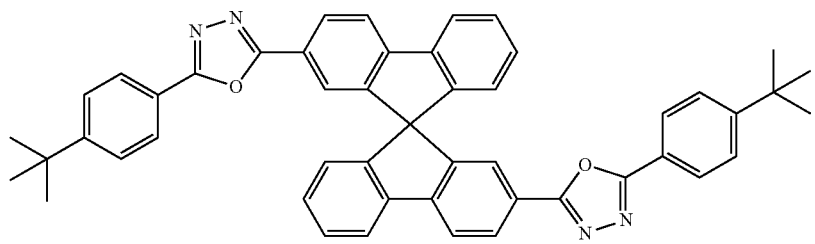
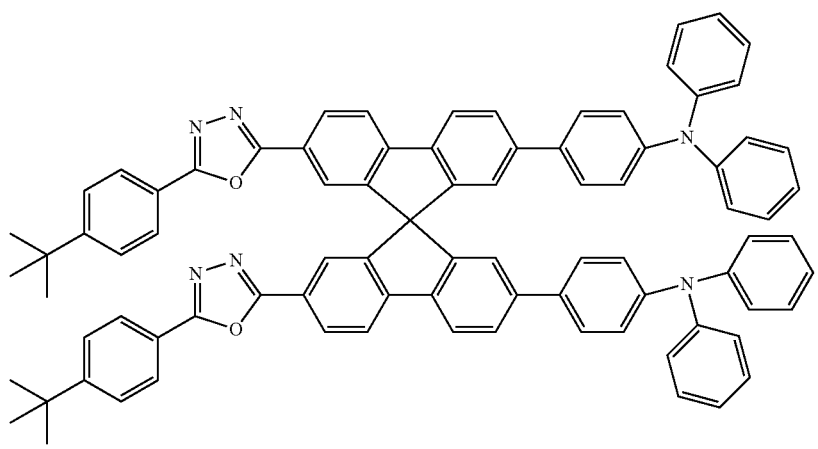

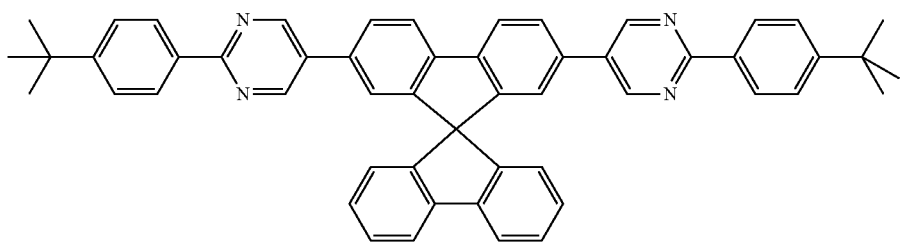
[Chemical Formula 51]
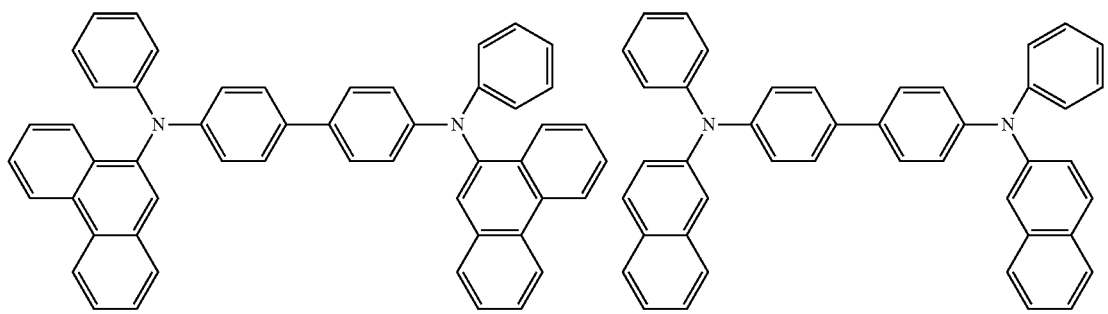
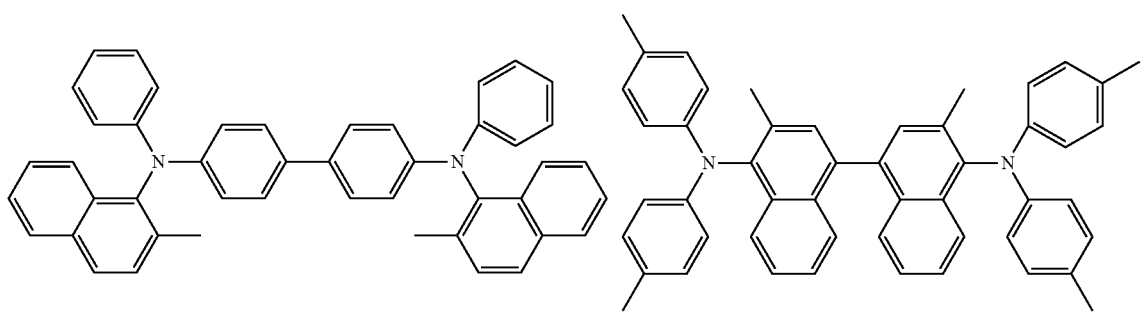
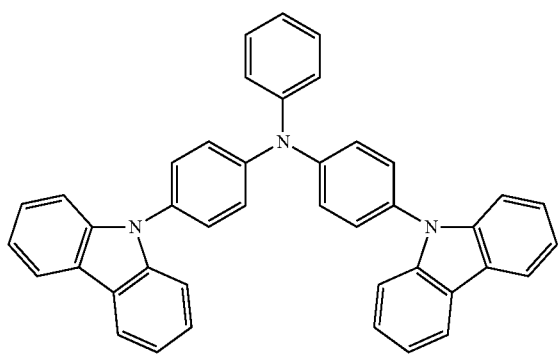

-continued
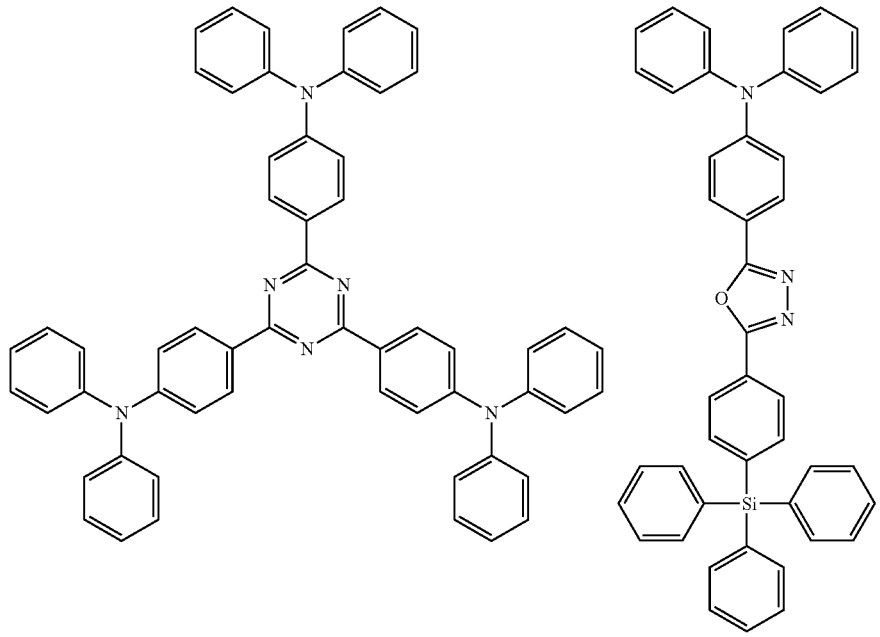
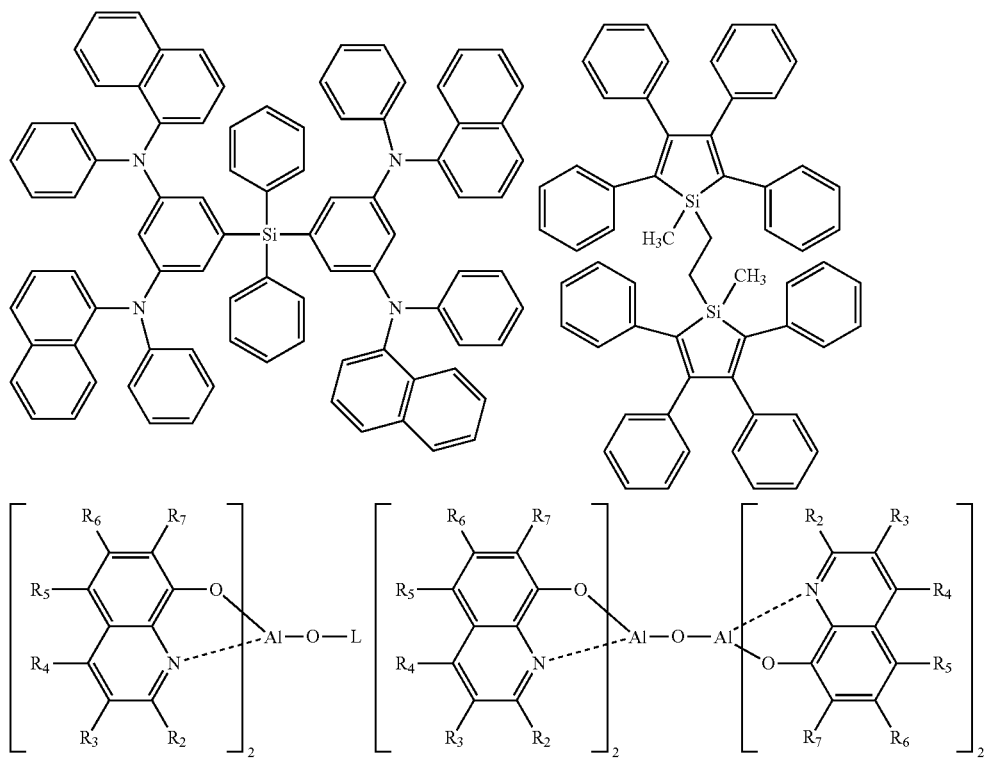
[Chemical Formula 52]
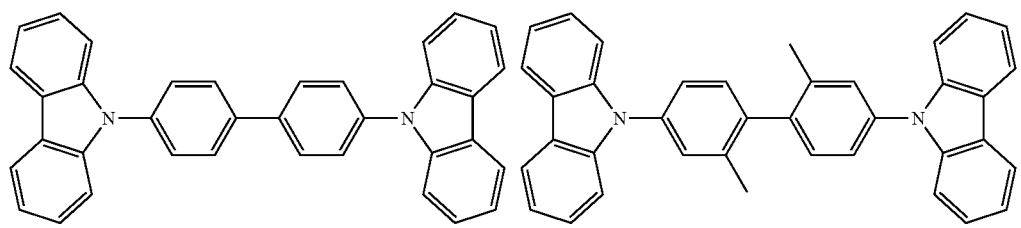

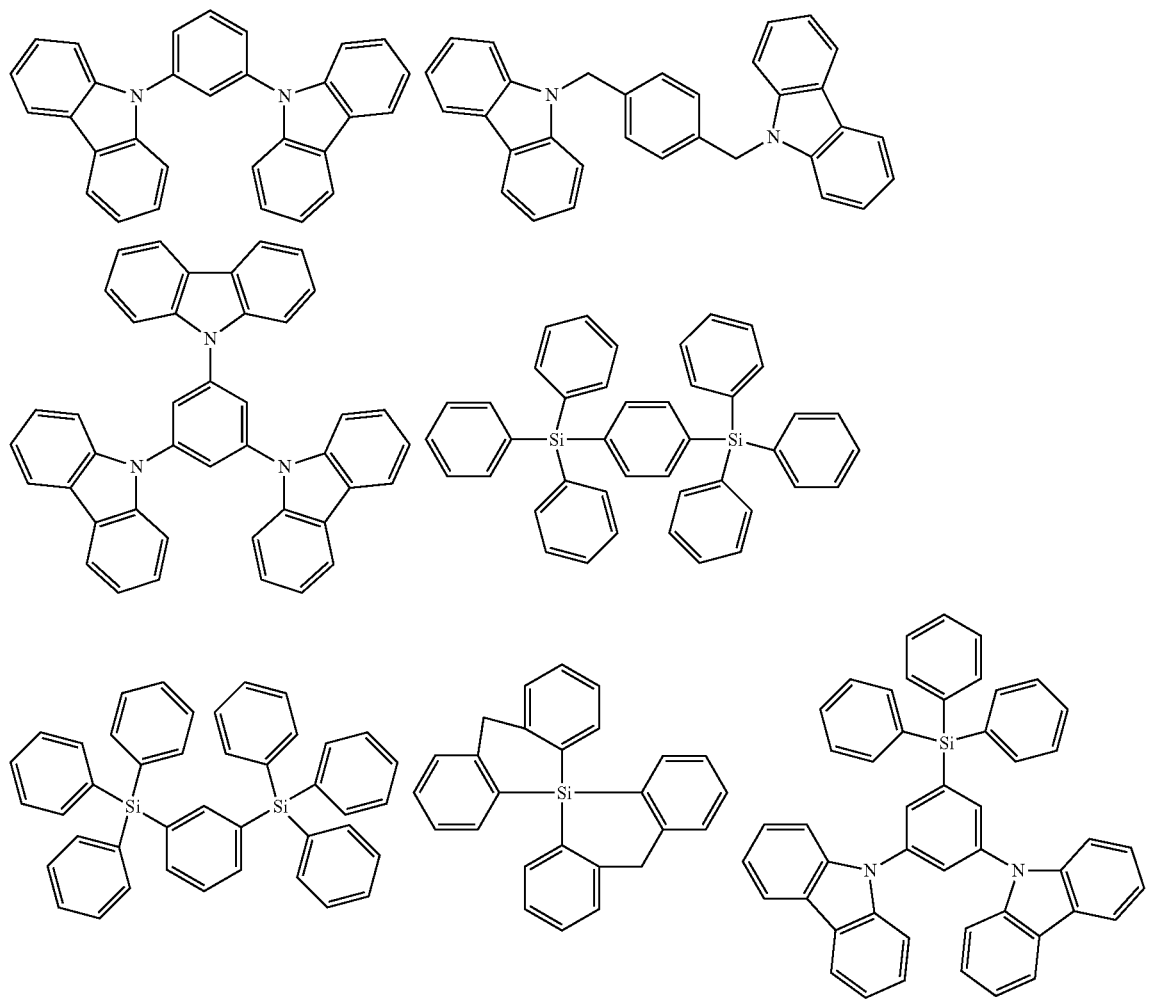
[Chemical Formula 53]
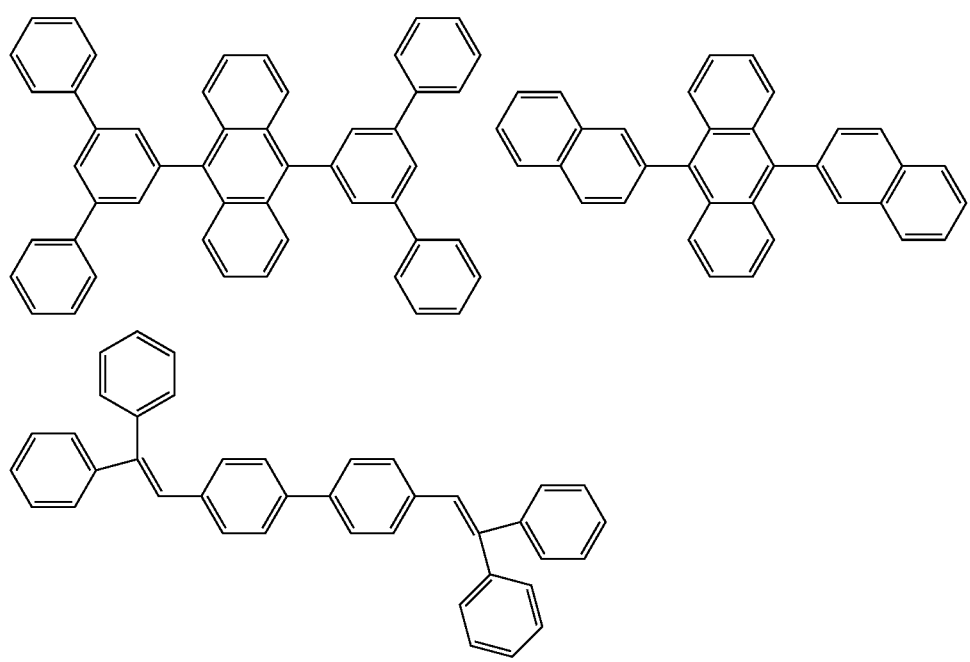

-continued
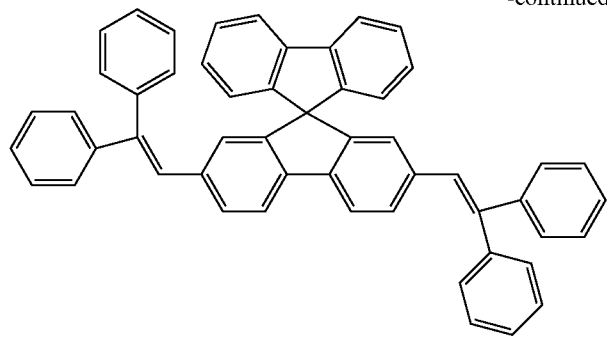
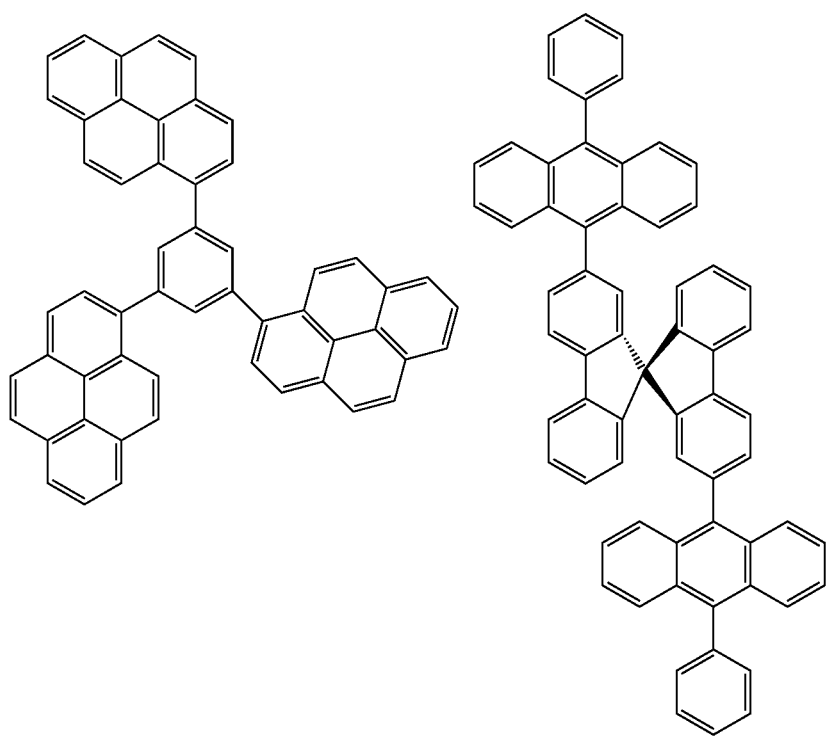
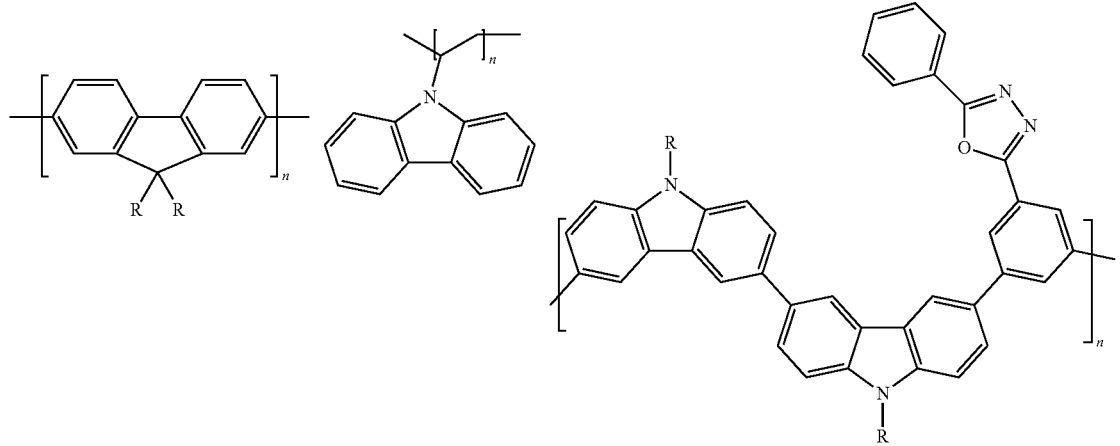

[Chemical Formula 54]
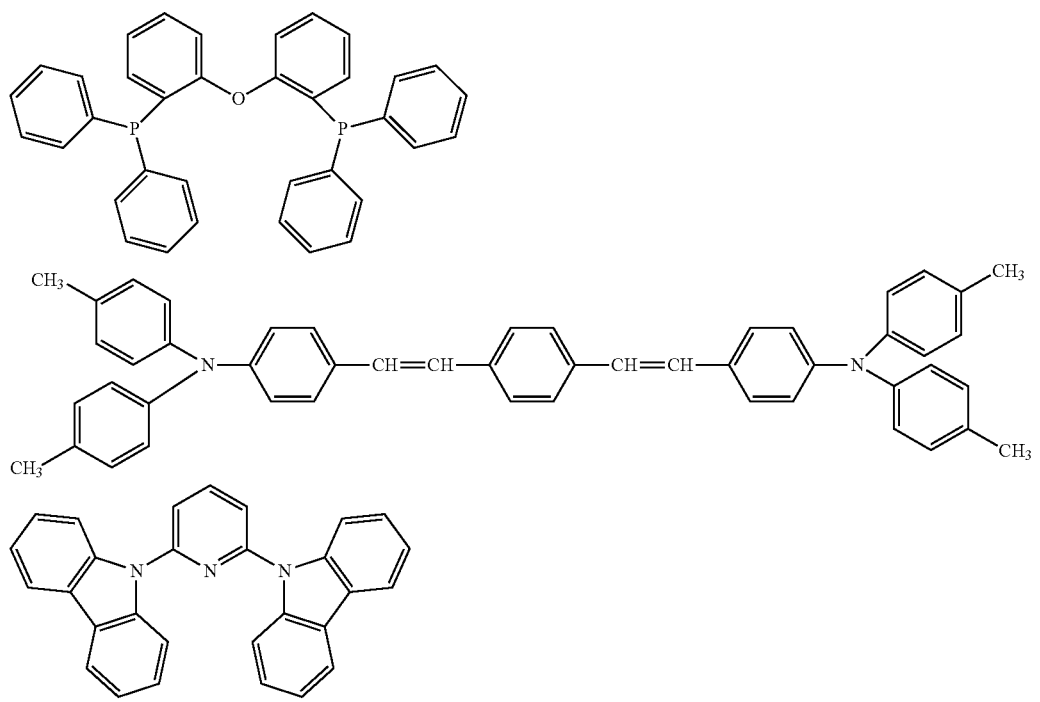
Preferred examples of a compound that may also be used as the material of the hole injection layer are shown below.
[Chemical Formula 55]
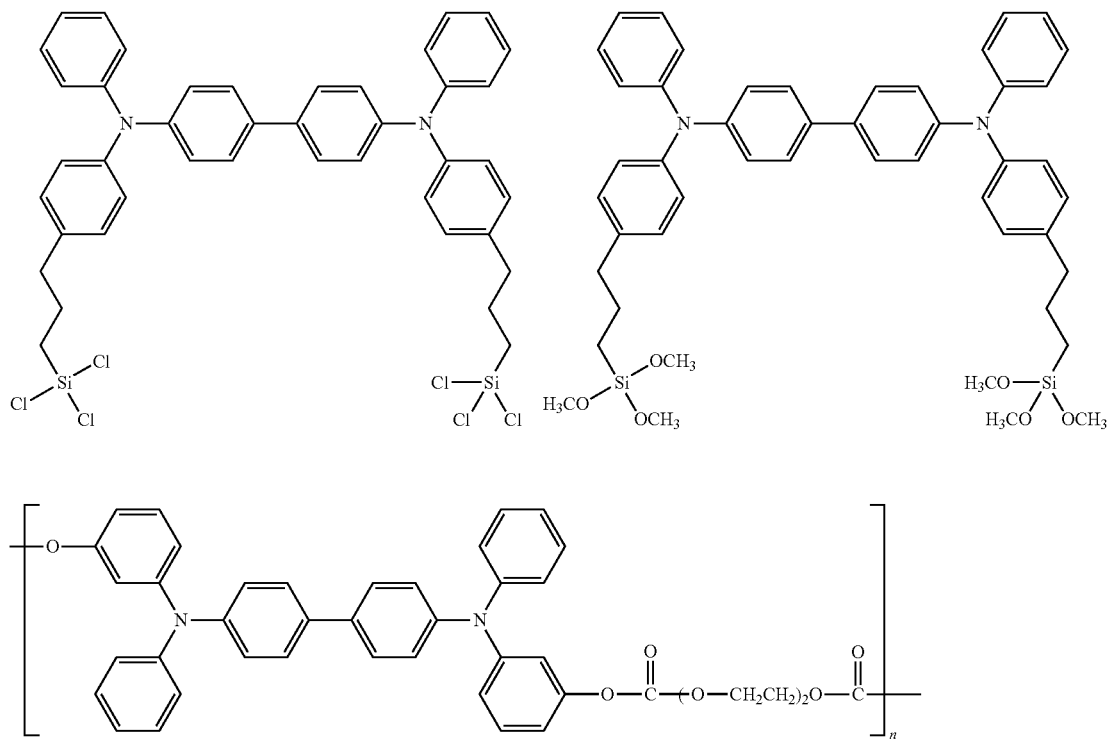

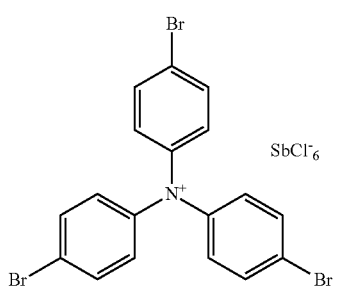
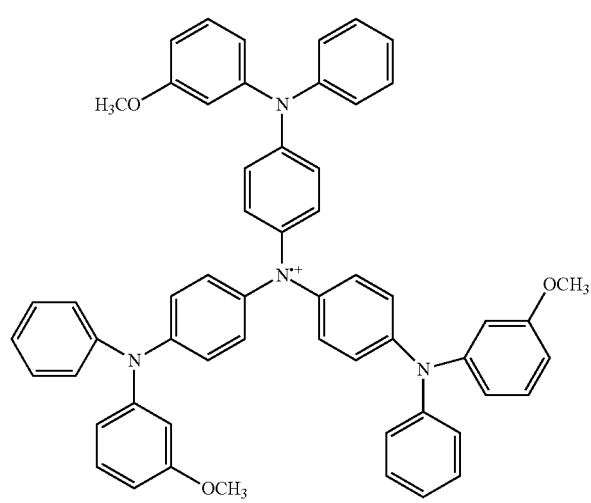
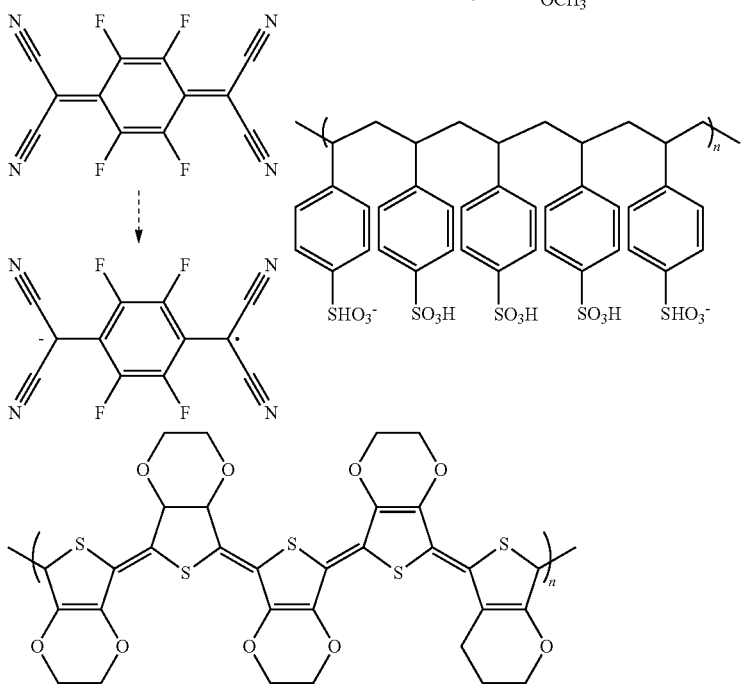
Preferred examples of a compound that may also be used as the material of the hole transport layer are shown below.
[Chemical Formula 56]
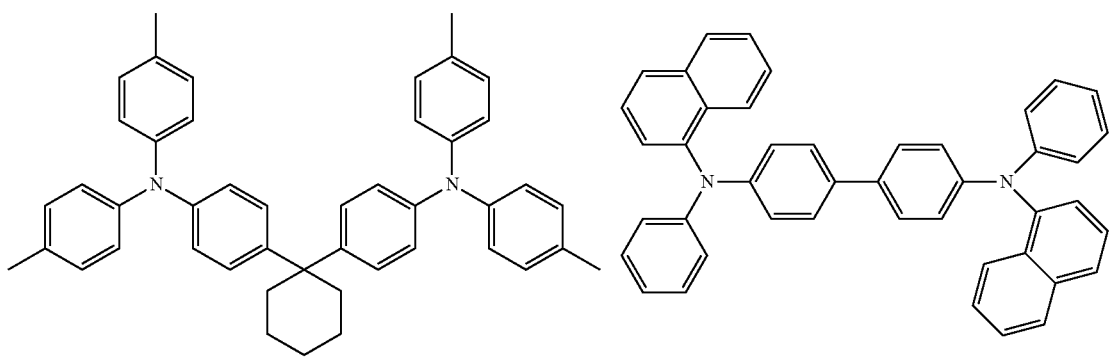

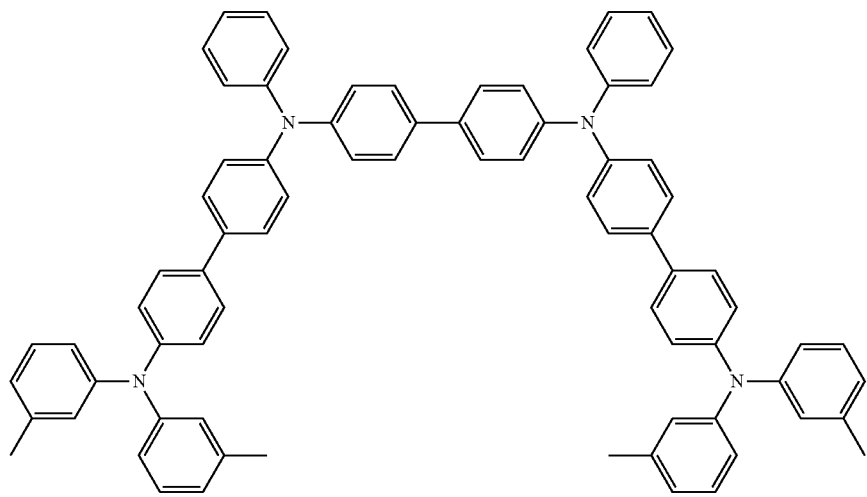
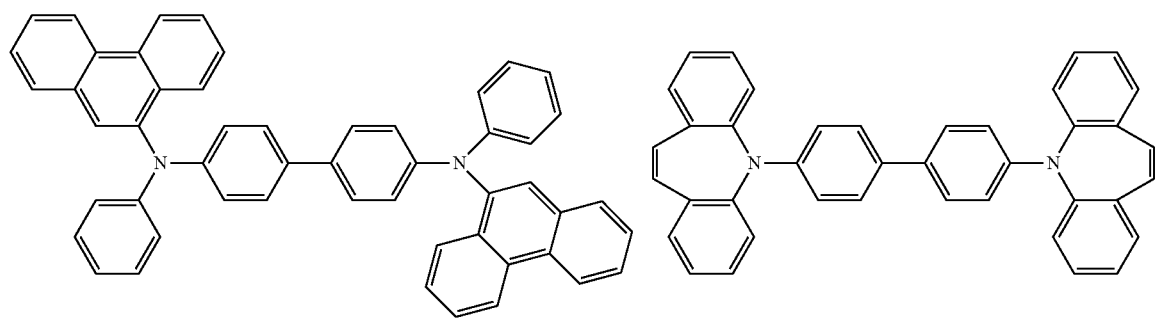
[Chemical Formula 57]
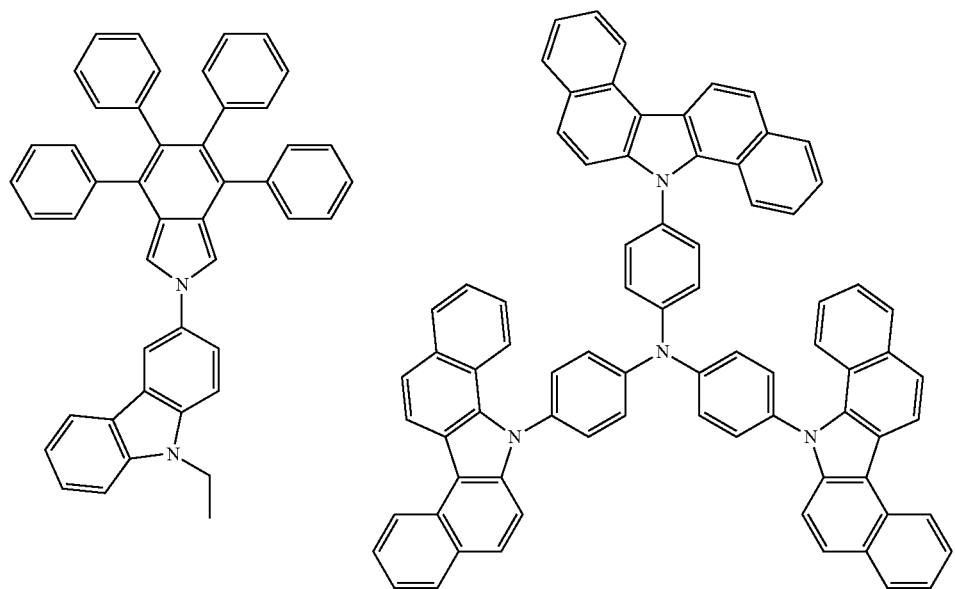

-continued
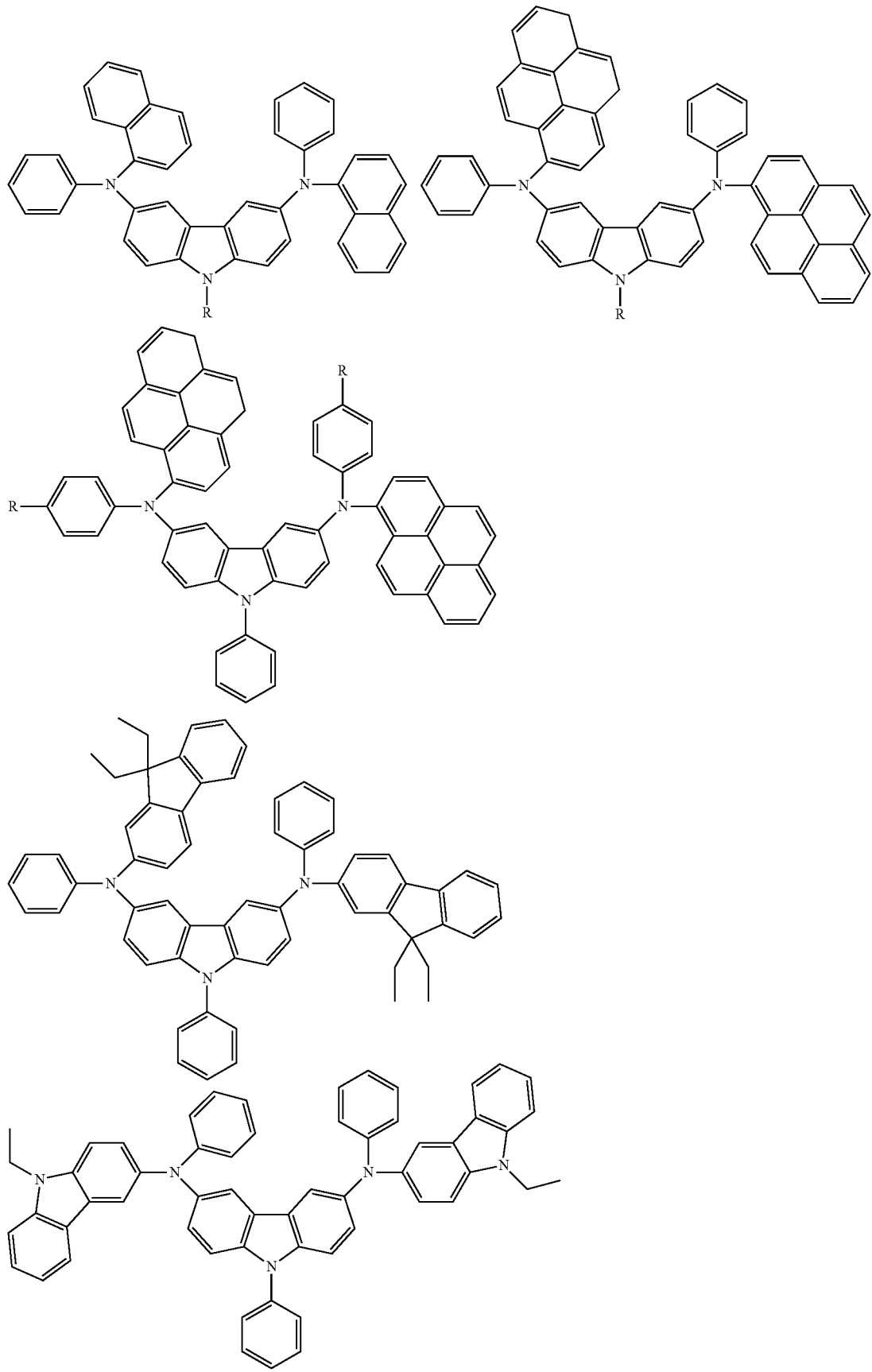

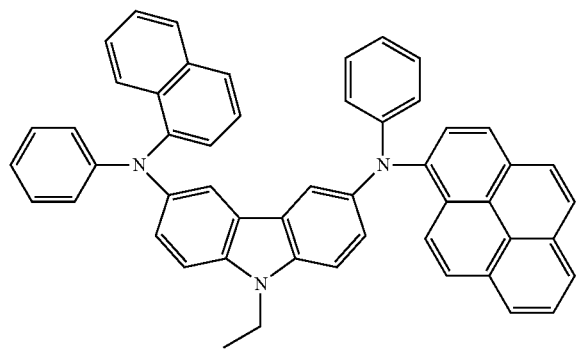
[Chemical Formula 58]
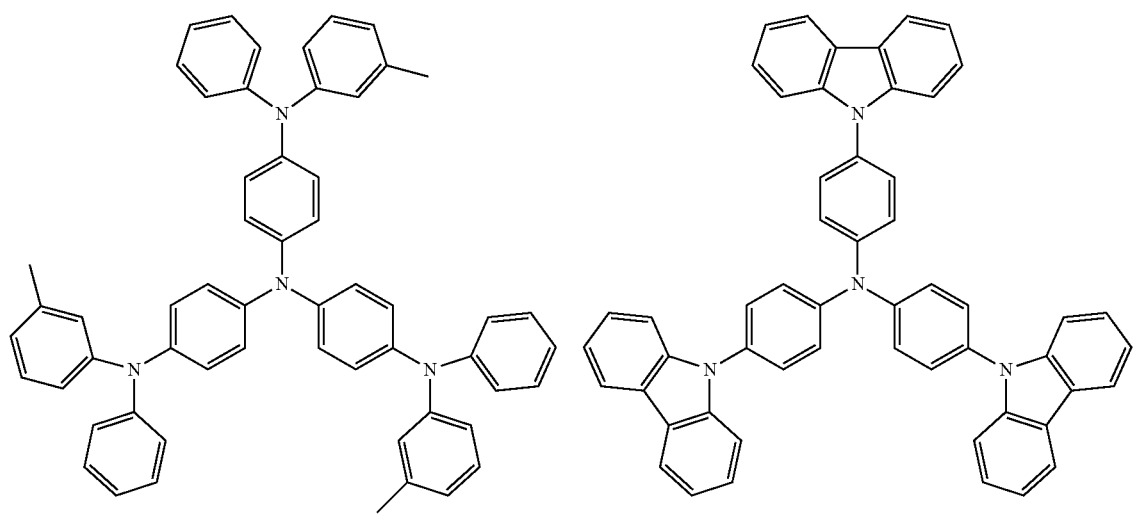
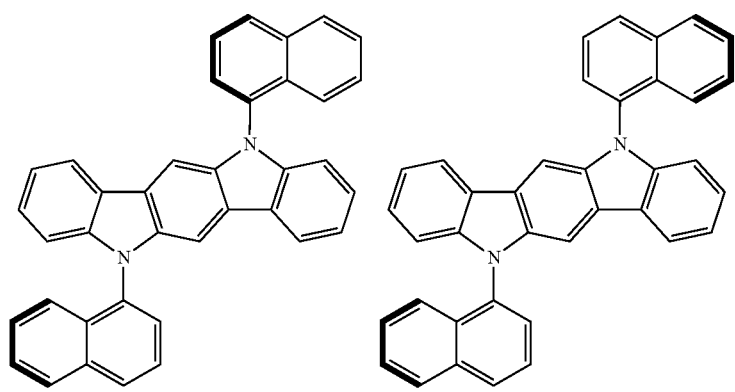

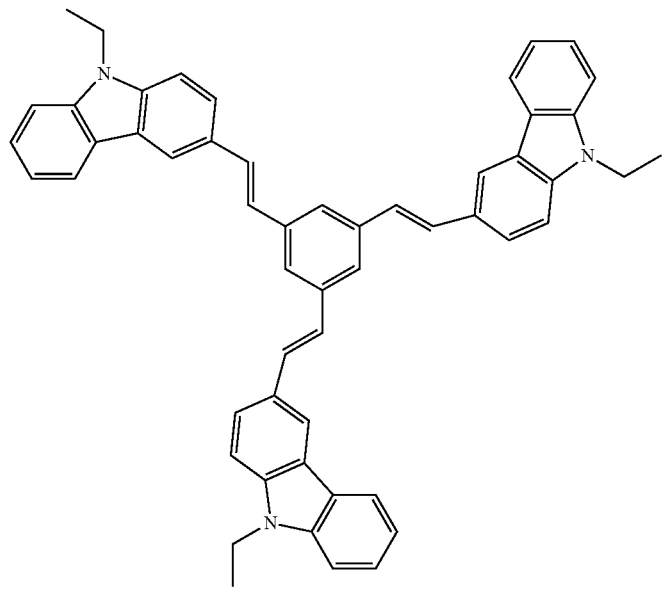
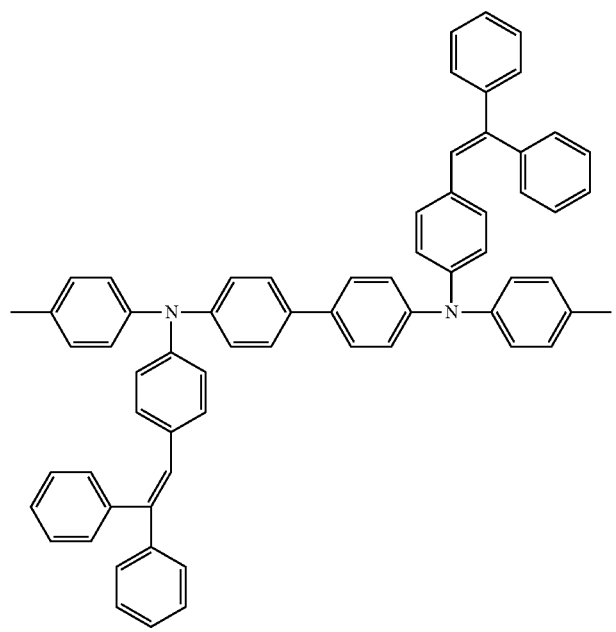
[Chemical Formula 59]
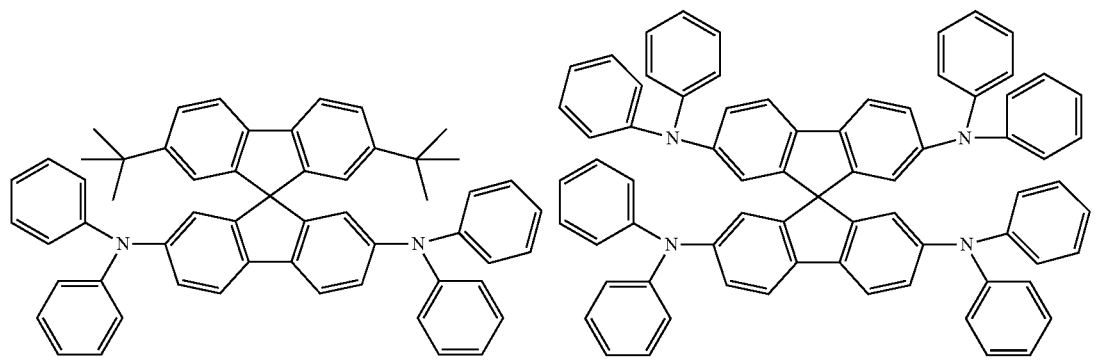

-continued
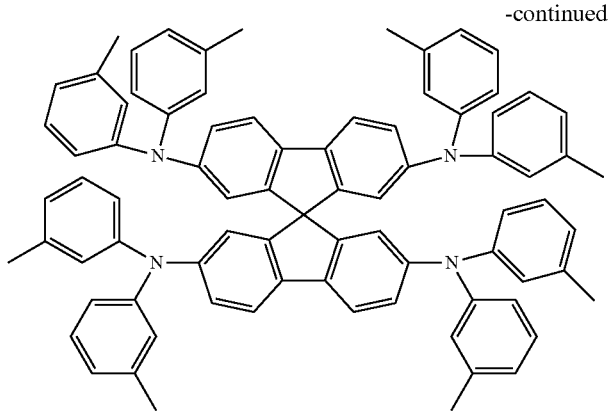
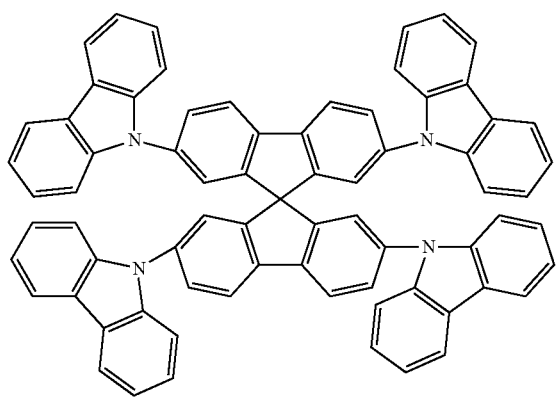
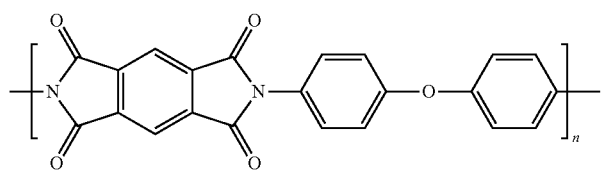
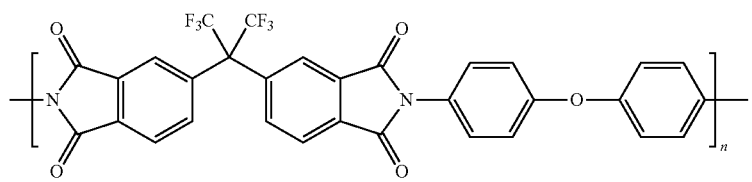
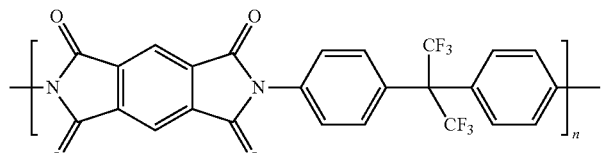
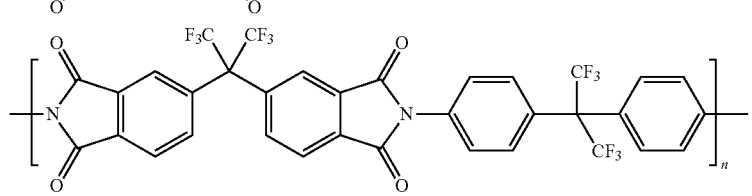

[Chemical Formula 60]
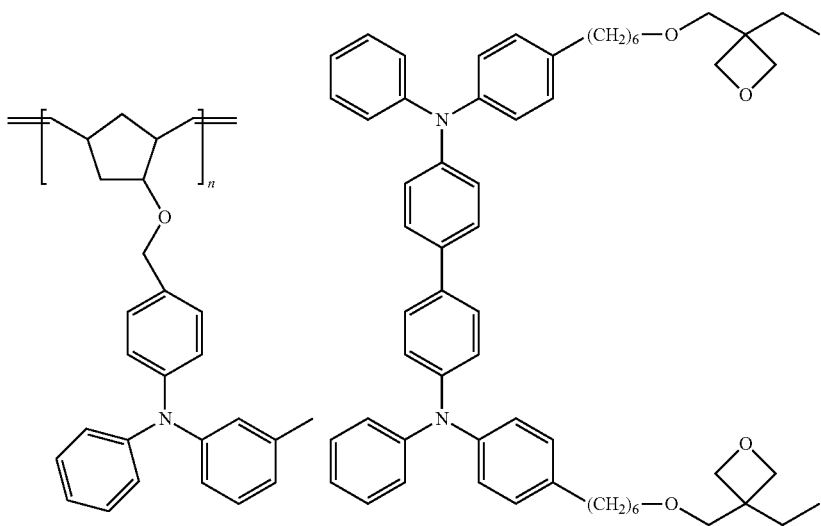
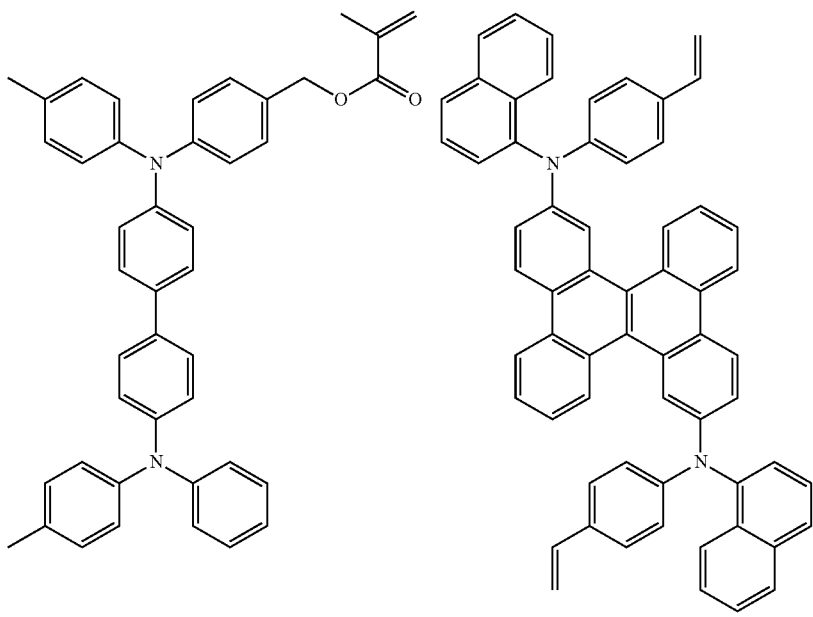
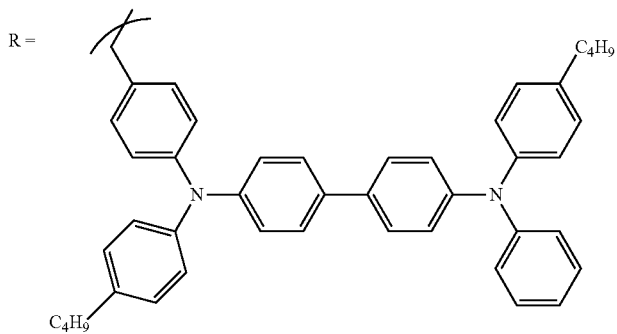

[Chemical Formula 61]
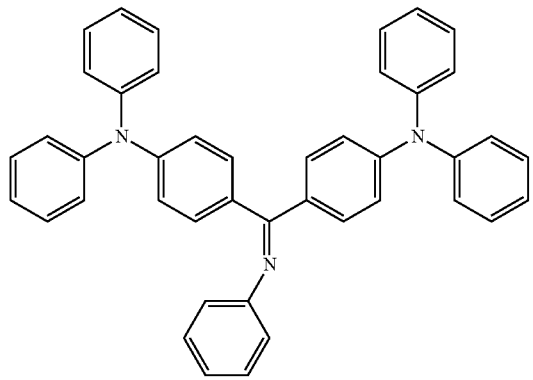
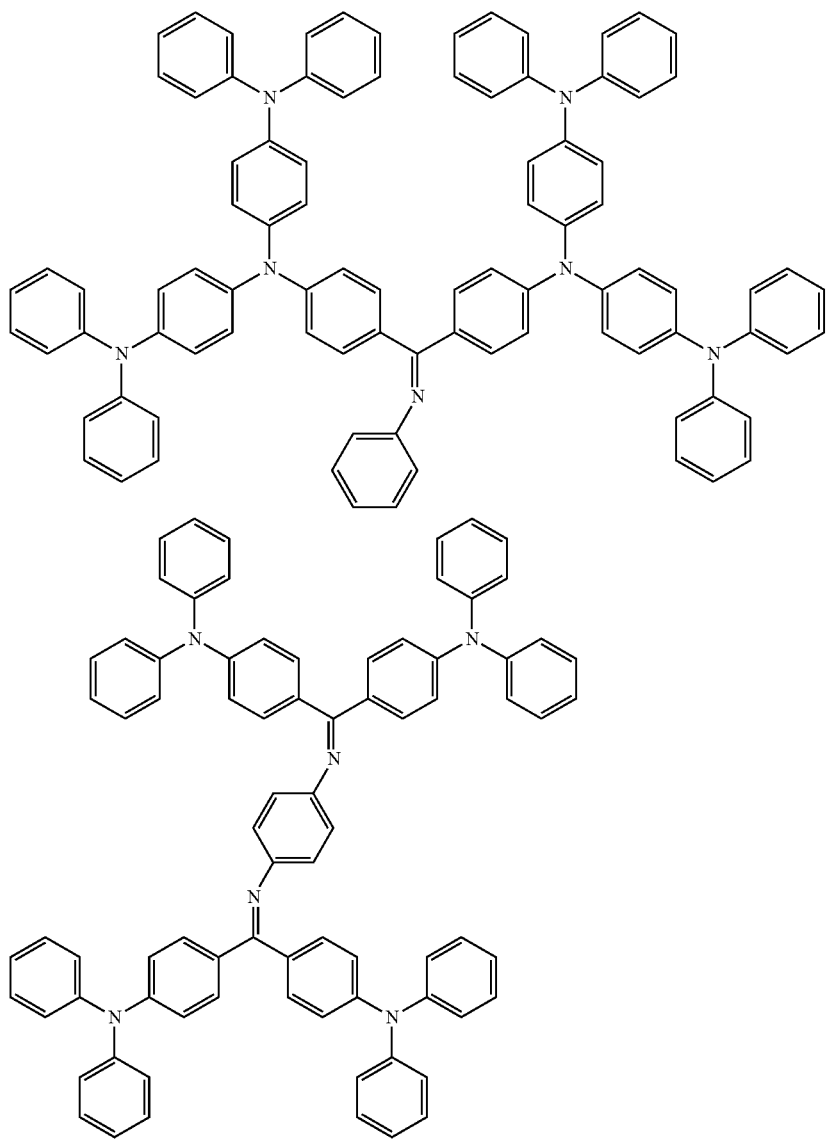

-continued
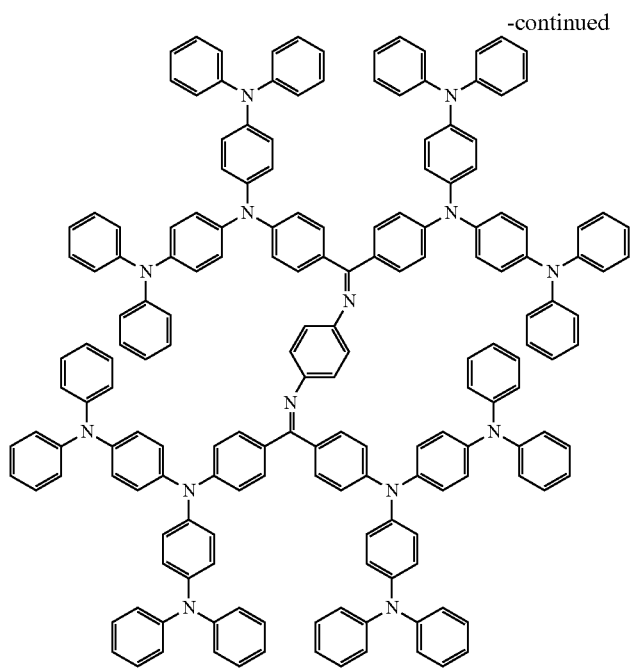
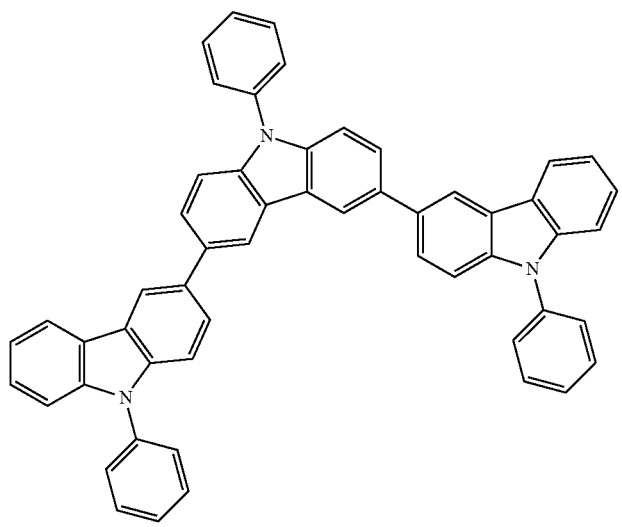
Preferred examples of a compound that may also be used as the material of the electron blocking layer are shown below.
[Chemical Formula 62]
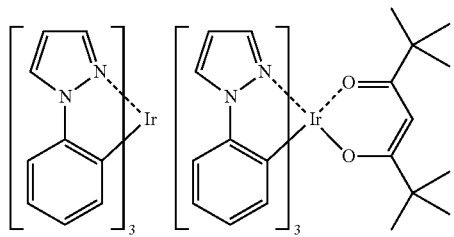
-continued
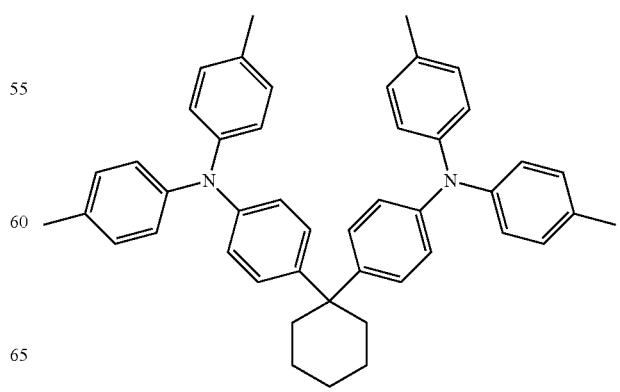

Preferred examples of a compound that may also be used as the material of the hole blocking layer are shown below.
[Chemical Formula 63]
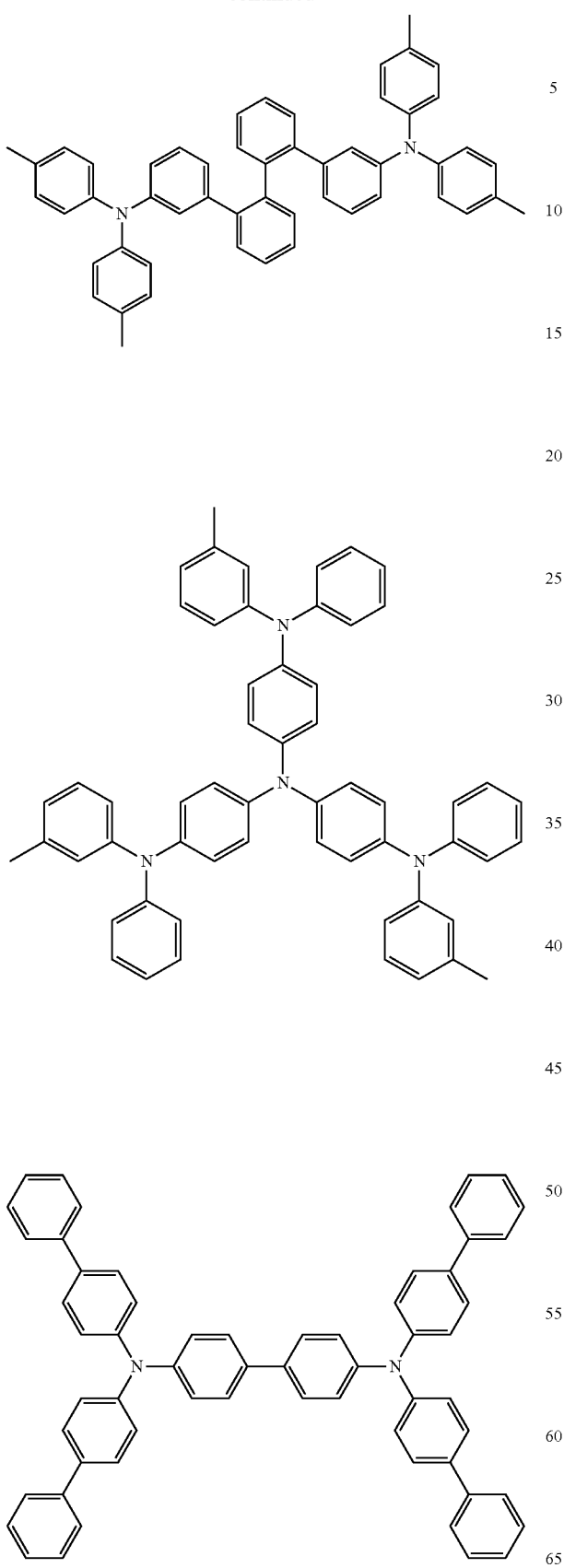
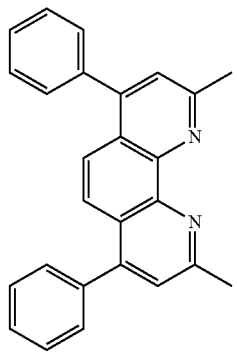
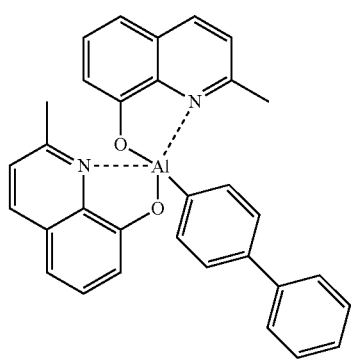
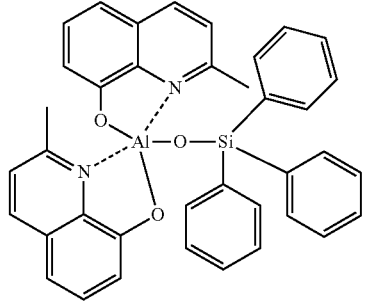
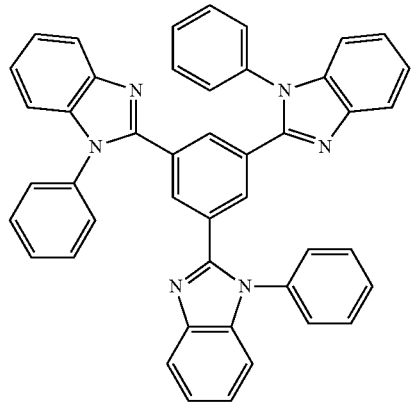

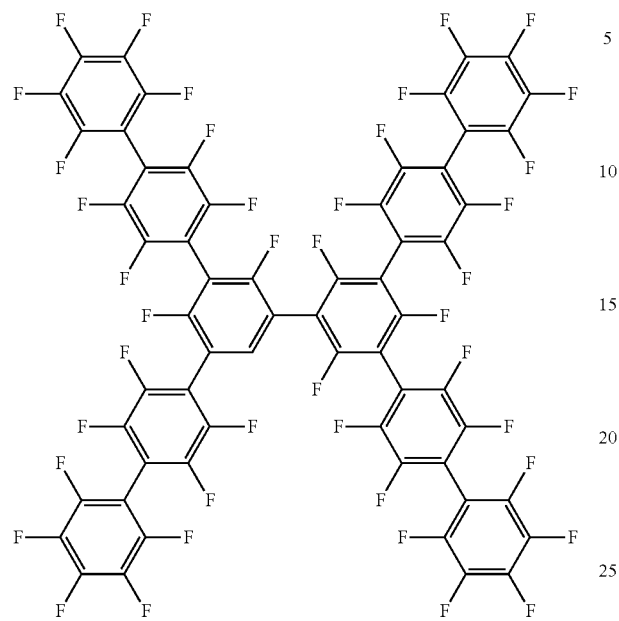
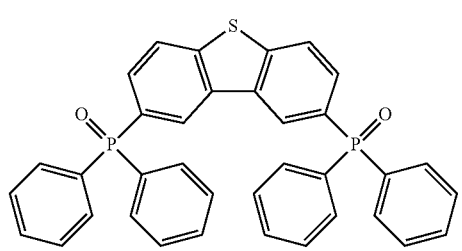
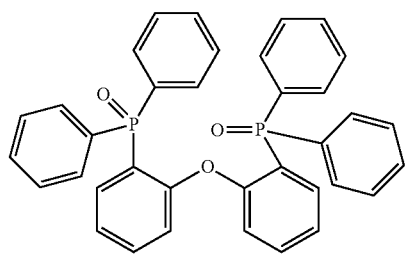
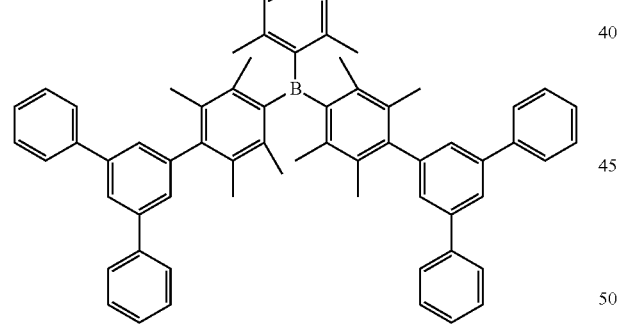
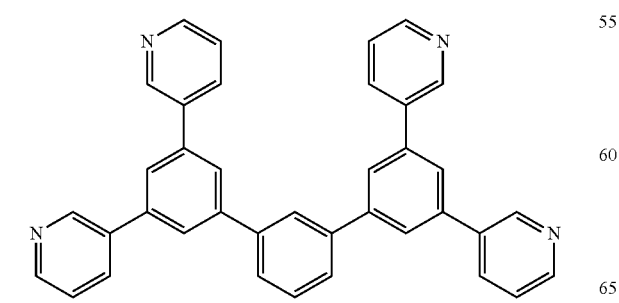
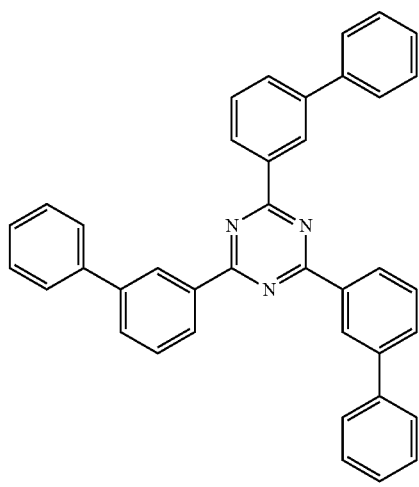

Preferred examples of a compound that may also be used as the material of the electron transport layer are shown below.
[Chemical Formula 64]
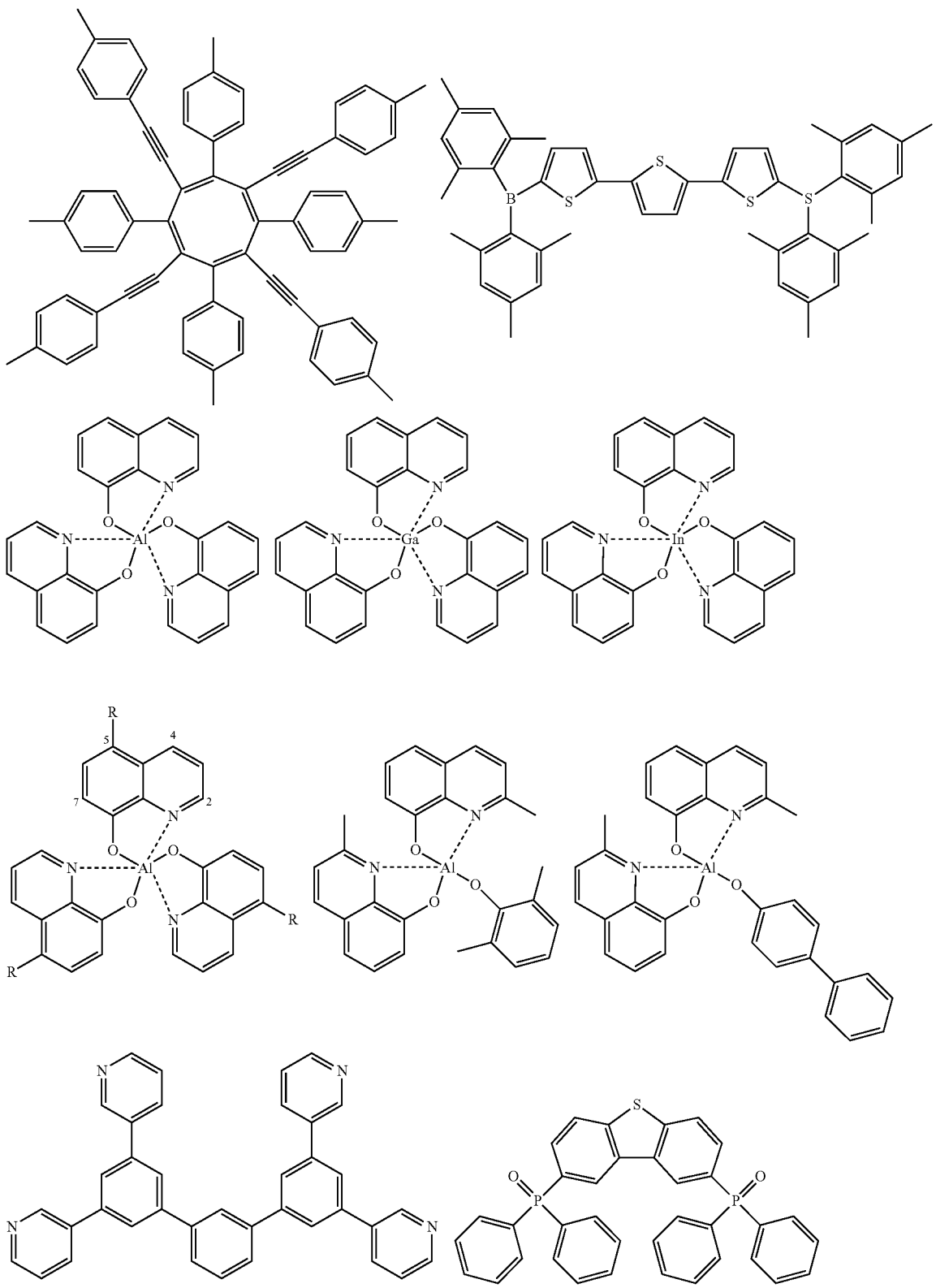

-continued
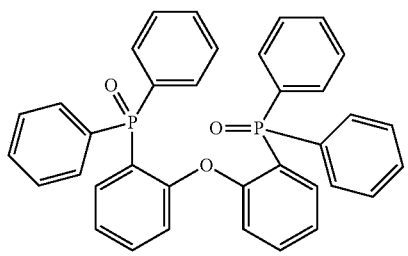
[Chemical Formula 65]
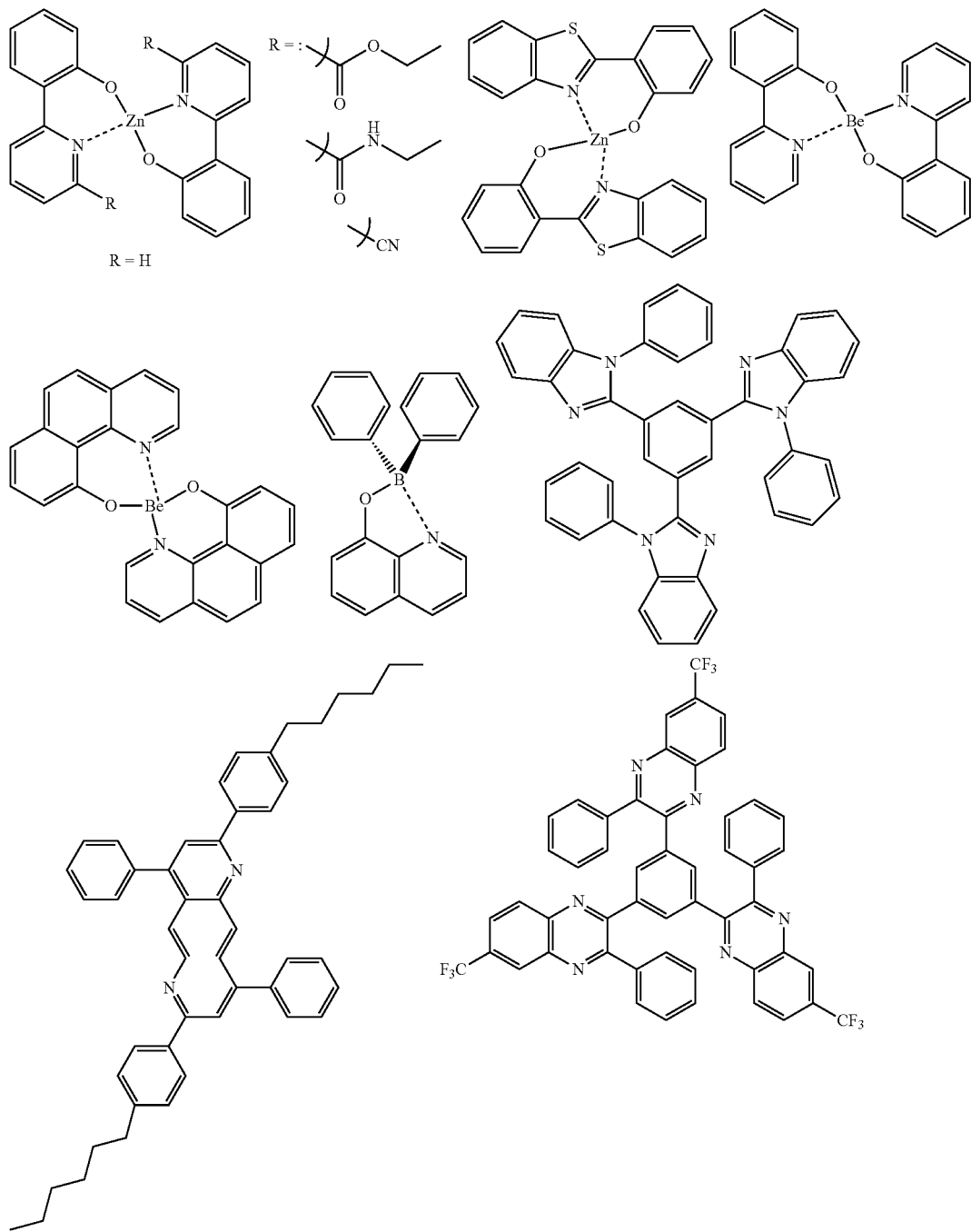

-continued
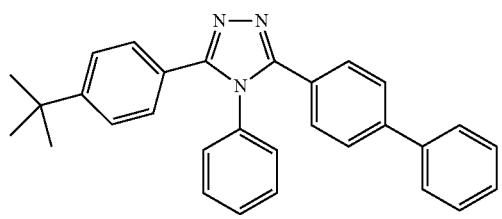
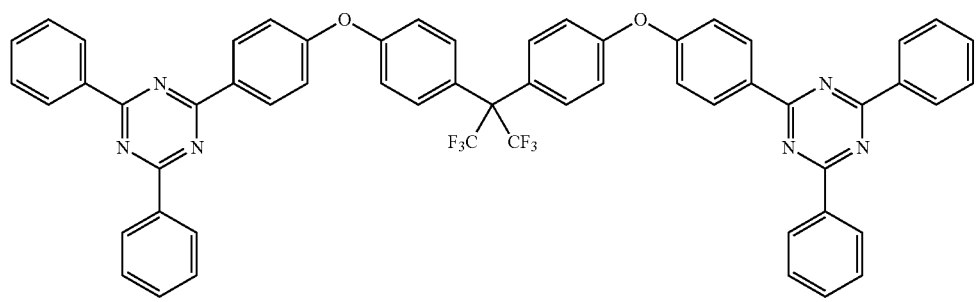
[Chemical Formula 66]
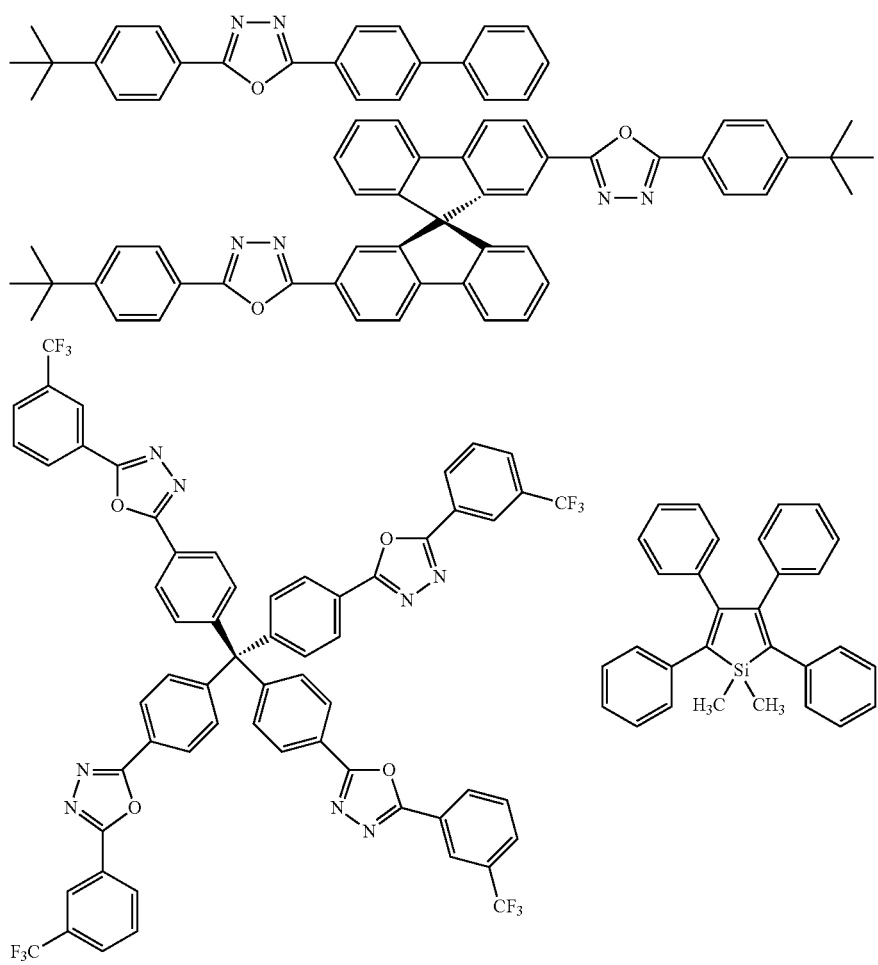

-continued
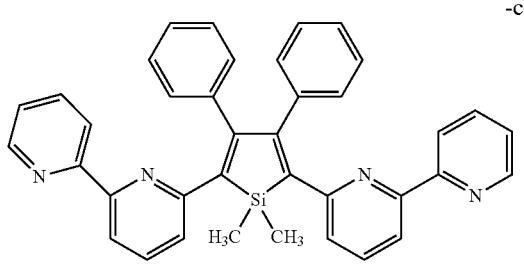
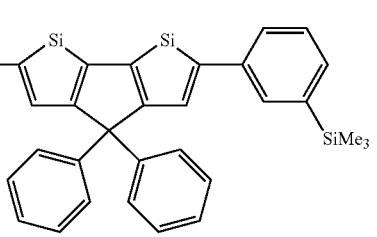
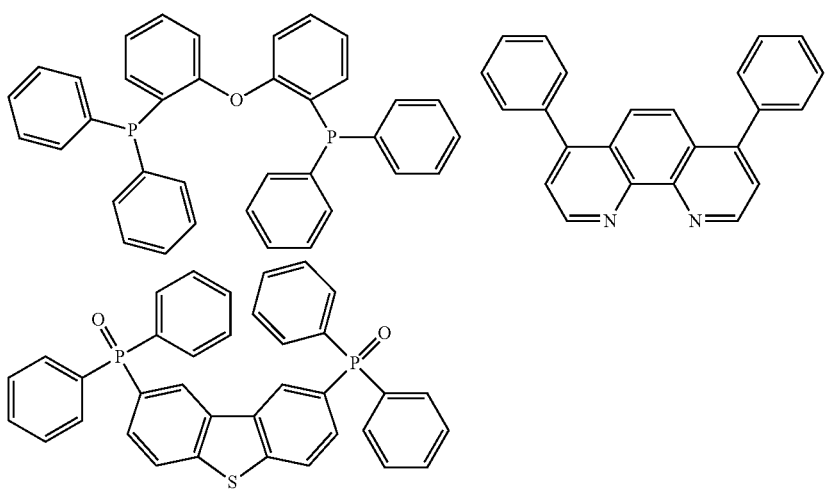
Preferred examples of a compound that may also be used as the material of the electron injection layer are shown below.
[Chemical Formula 67]
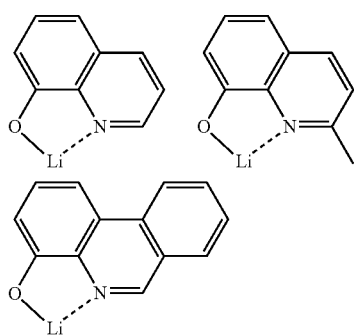
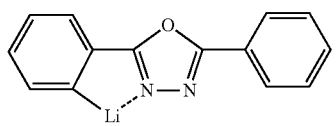
Preferred examples of a compound as a material that may be added are shown below. For example, the compound may be added as a stabilizing material.
[Chemical Formula 68]
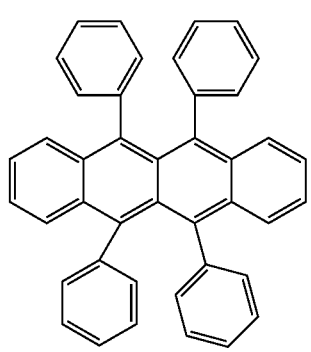
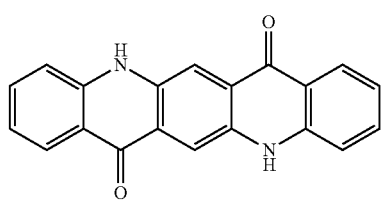

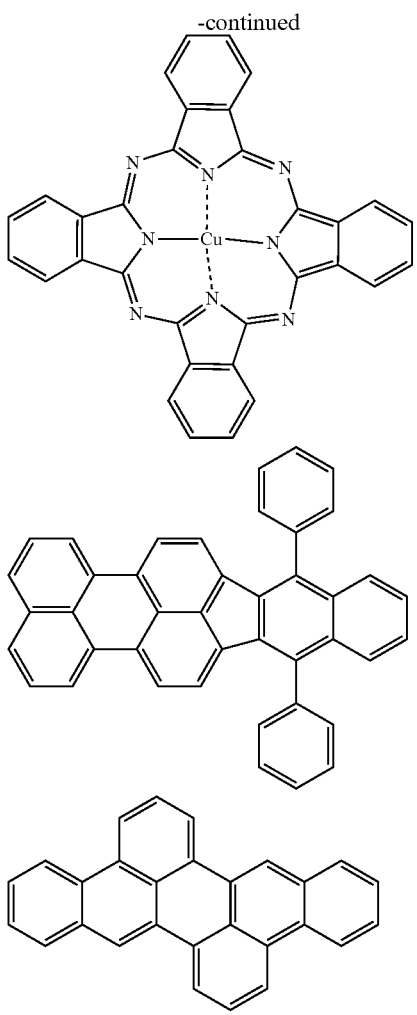

The following describes an embodiment of the present invention in more detail based on Examples. The present invention, however, is not restricted to the following Examples, as long as such departures are within the scope of the invention.

Example 1

Synthesis of [3'-[2-{3-(9H-carbazol-9-yl)phenyl}-9H-carbazol-9-yl]biphenyl-3-yl]-3,5-diphenyl-1,3,5-triazine (Compound 6)

To a reaction vessel having been substituted with nitrogen, 2-hydroxycarbazole (5.0 g) and pyridine (100 mL) were added, to which trifluoromethanesulfonic anhydride (12.0 g) was added dropwise at 0° C. under stirring. The temperature was increased to room temperature, and after stirring for 3 hours, water and chloroform were added thereto, and an organic layer was collected through extraction. After distilling off the solvent, the product was purified by column chromatography, thereby providing a white solid matter of 2-trifluoromethanesulfonyloxycarbazole (yield: 83%).

2-Trifluoromethanesulfonyloxycarbazole (5.8 g) thus obtained, 3-(9H-carbazol-9-yl)phenylboronic acid (5.0 g), potassium carbonate (3.6 g), toluene (100 mL), ethanol (25 mL), and water (25 mL) were added to a reaction vessel having been substituted with nitrogen, and then tetrakis (triphenylphosphine) palladium (2.0 g) was added thereto under a nitrogen stream, followed by heating under refluxing for 3 hours under stirring. After allowing the reaction mixture to cool to room temperature, water and ethyl acetate were added thereto, and an organic layer was collected through extraction. After distilling off the solvent, the product was purified by column chromatography, thereby providing a white solid matter of 2-{3-(9H-carbazol-9-yl)phenyl}-9H-carbazole (yield: 82%).

Separately, to a reaction vessel having been substituted with nitrogen, 3'-bromobiphenyl-3-carboxylic acid (5.0 g) and thionyl chloride (20 mL) were added and heated under refluxing for 1 hour. After distilling off thionyl chloride, the reaction mixture was allowed to cool, and dichloromethane (100 mL), benzonitrile (3.8 mL), and antimony(V) chloride (5.4 g) were added thereto, followed by heating under refluxing for 3 hours under stirring. After allowing the reaction mixture to cool to room temperature, an orange solid matter formed was collected by filtration. After rinsing the product with dichloromethane, the product was added gradually to aqueous ammonia (180 mL), and the mixture was stirred for 1 hour under cooling to 0° C. The product was collected by filtration, thereby providing a white solid matter of 3'-(bromobiphenyl-3-yl)-3,5-diphenyl-1,3,5-triazine (yield: 55%).

2-{3-(9H-Carbazol-9-yl)phenyl}-9H-carbazole (0.88 g) and 3'-(bromobiphenyl-3-yl)-3,5-diphenyl-1,3,5-triazine (1.0 g) thus obtained were added to a reaction vessel having been substituted with nitrogen, to which tri-tert-butylphosphine (0.09 g), tert-butoxy sodium (0.23 g), and xylene (60 mL) were further added, and subsequently tris(dibenzylideneacetone) dipalladium chloroform inclusion complex (0.07 g) was further added, and the reaction mixture was heated under refluxing for 3 hours under stirring. After cooling to room temperature, a saturated sodium chloride aqueous solution (100 mL) and ethyl acetate (50 mL) were added thereto, and an organic layer was collected through extraction. After distilling off the solvent, the product was purified by column chromatography, thereby providing a white solid matter of [3'-[2-{3-(9H-carbazol-9-yl)phenyl}-9H-carbazol-9-yl]biphenyl-3-yl]-3,5-diphenyl-1,3,5-triazine (Compound 6) (yield: 40%).

[Chemical Formula 69]

(Compound 6)

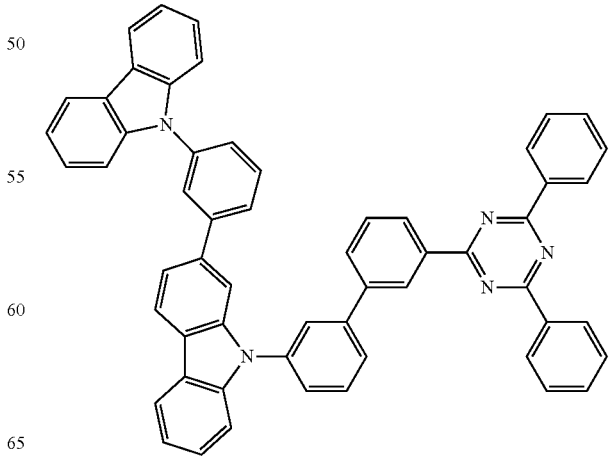

The structure of the obtained white solid was identified by NMR. The ¹H-NMR measurement result is presented in FIG. 1.

¹H-NMR (CDCl₃) detected 37 hydrogen signals, as follows.

δ (ppm)=7.21 (2H), 7.31 (3H), 7.38-7.68 (15H), 7.74 (3H), 7.82 (2H), 7.87 (1H), 7.97 (1H), 8.07 (2H), 8.18 (1H), 8.22 (1H), 8.63-8.80 (5H), 9.00 (1H).

Example 2

Synthesis of [4'-[2-{3-(9H-carbazol-9-yl)phenyl}-9H-carbazol-9-yl]biphenyl-3-yl]-3,5-diphenyl-1,3,5-triazine (Compound 3)

To a reaction vessel having been substituted with nitrogen, 4'-bromobiphenyl-3-carboxylic acid (5.0 g) and thionyl chloride (20 mL) were added and heated under refluxing for 1 hour. After distilling off thionyl chloride, the reaction mixture was allowed to cool, and dichloromethane (100 mL), benzonitrile (3.8 mL), and antimony(V) chloride (5.4 g) were added thereto, followed by heating under refluxing for 3 hours under stirring. After allowing the reaction mixture to cool to room temperature, an orange solid matter formed was collected by filtration. After rinsing the product with dichloromethane, the product was added gradually to aqueous ammonia (180 mL), and the mixture was stirred for 1 hour under cooling to 0° C. The product was collected by filtration, thereby providing a white solid matter of (4'-bromobiphenyl-3-yl)-3,5-diphenyl-1,3,5-triazine (yield: 53%).

(4'-Bromobiphenyl-3-yl)-3,5-diphenyl-1,3,5-triazine (1.0 g) thus obtained and 2-{3-(9H-carbazol-9-yl)phenyl}-9H-carbazole (0.88 g) synthesized in Example 1 were added to a reaction vessel having been substituted with nitrogen, to which tri-tert-butylphosphine (0.09 g), tert-butoxy sodium (0.23 g), and xylene (60 mL) were further added, and subsequently tris(dibenzylideneacetone) dipalladium chloroform inclusion complex (0.07 g) was further added, and the reaction mixture was heated under refluxing for 3 hours under stirring. After cooling to room temperature, a saturated sodium chloride aqueous solution (100 mL) and ethyl acetate (50 mL) were added thereto, and an organic layer was collected through extraction. After distilling off the solvent, the product was purified by column chromatography, thereby providing a white solid matter of [4'-[2-{3-(9H-carbazol-9-yl)phenyl}-9H-carbazol-9-yl]biphenyl-3-yl]-3,5-diphenyl-1,3,5-triazine (Compound 3) (yield: 35%).

[Chemical Formula 70]

(Compound 3)

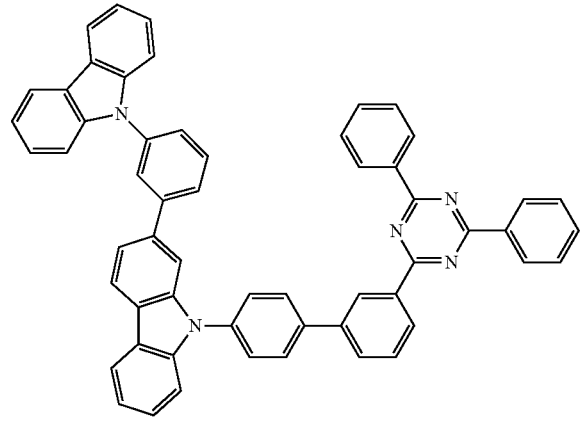

Figure 2:
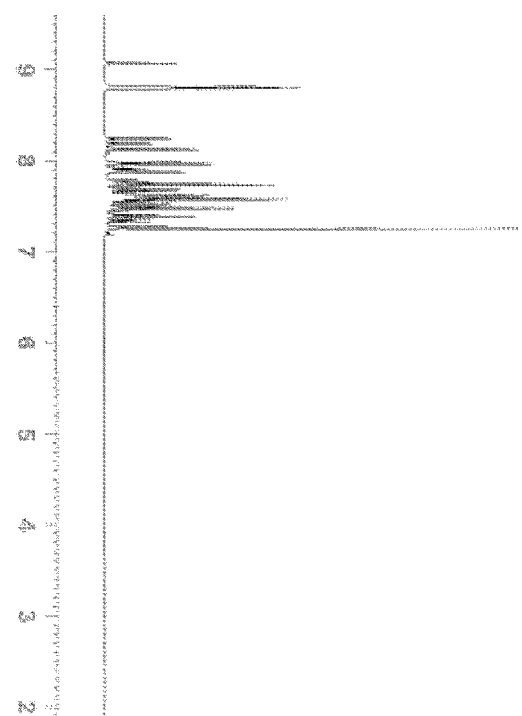
FIG. 2 is a $^1$H-NMR chart of the compound (compound 3) of Example 2 of the present invention.

The structure of the obtained white solid was identified by NMR. The ¹H-NMR measurement result is presented in FIG. 2.

¹H-NMR (CDCl₃) detected 37 hydrogen signals, as follows.

δ (ppm)=7.18-7.85 (24H), 7.85-7.95 (2H), 7.94 (1H), 8.13 (2H), 8.19 (1H), 8.24 (1H), 8.74-8.85 (5H), 9.08 (1H).

Example 3

Synthesis [3'-[2-{3-(9H-carbazol-9-yl)phenyl}-9H-carbazol-9-yl]biphenyl-4-yl]-3,5-diphenyl-1,3,5-triazine (Compound 5)

To a reaction vessel having been substituted with nitrogen, 4-iodobenzoic acid (5.0 g) and thionyl chloride (50 mL) were added and heated under refluxing for 1 hour. After distilling off thionyl chloride, the reaction mixture was allowed to cool, and dichloromethane (100 mL), benzonitrile (4.2 mL), and antimony(V) chloride (6.0 g) were added thereto, followed by heating under refluxing for 3 hours under stirring. After allowing the reaction mixture to cool to room temperature, an orange solid matter formed was collected by filtration. After rinsing the product with dichloromethane, the product was added gradually to aqueous ammonia (180 mL), and the mixture was stirred for 1 hour under cooling to 0° C. The product was collected by filtration, thereby providing a white solid matter of 4-iodophenyl-3,5-diphenyl-1,3,5-triazine (yield: 84%).

4-Iodophenyl-3,5-diphenyl-1,3,5-triazine (5.0 g) thus obtained, 3-bromophenylboronic acid (2.5 g), potassium carbonate (1.9 g), toluene (100 mL), ethanol (20 mL), and water (20 mL) were added to a reaction vessel having been substituted with nitrogen, and then tetrakis(triphenylphosphine) palladium (1.3 g) was added thereto under a nitrogen stream, followed by heating under refluxing for 3 hours under stirring. After allowing the reaction mixture to cool to room temperature, water and toluene were added thereto, and an organic layer was collected through extraction. After distilling off the solvent, the product was purified by column chromatography, thereby providing a white solid matter of (3'-bromobiphenyl-4-yl)-3,5-diphenyl-1,3,5-triazine (yield: 44%).

(3'-Bromobiphenyl-4-yl)-3,5-diphenyl-1,3,5-triazine (1.0 g) thus obtained and 2-{3-(9H-carbazol-9-yl)phenyl}-9H-carbazole (0.88 g) synthesized in Example 1 were added to a reaction vessel having been substituted with nitrogen, to which tri-tert-butylphosphine (0.09 g), tert-butoxy sodium (0.23 g), and xylene (60 mL) were further added, and subsequently tris(dibenzylideneacetone) dipalladium chloroform inclusion complex (0.07 g) was further added, and the reaction mixture was heated under refluxing for 3 hours under stirring. After cooling to room temperature, a saturated sodium chloride aqueous solution (100 mL) and ethyl acetate (50 mL) were added thereto, and an organic layer was collected through extraction. After distilling off the solvent, the product was purified by column chromatography, thereby providing a white solid matter of [3'-[2-{3-(9H-carbazol-9-yl)phenyl}-9H-carbazol-9-yl]biphenyl-4-yl]-3,5-diphenyl-1,3,5-triazine (Compound 5) (yield: 35%).

[Chemical Formula 71]

(Compound 5)

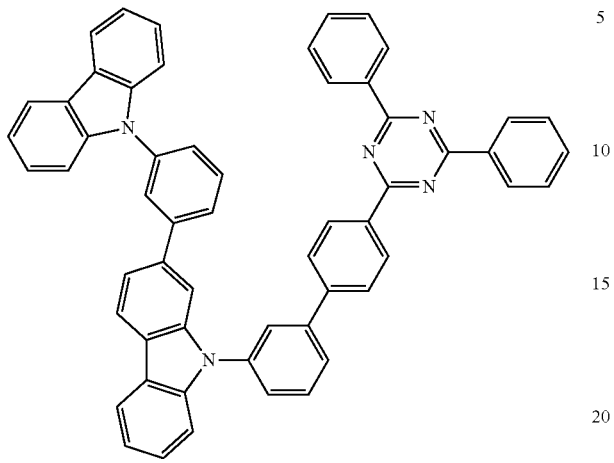

Figure 3:
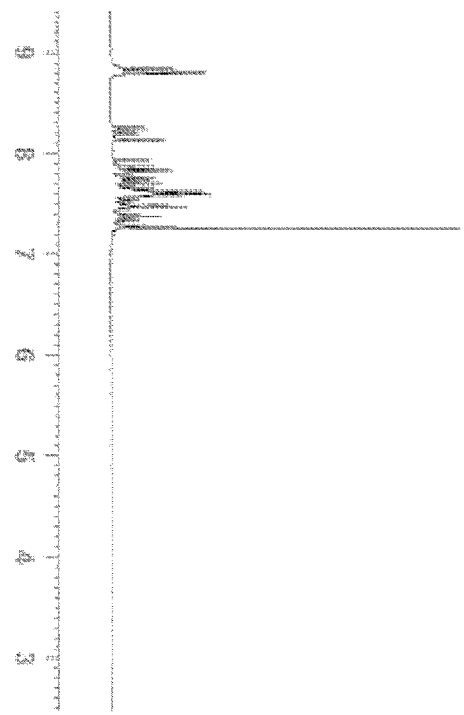
FIG. 3 is a $^1$H-NMR chart of the compound (compound 5) of Example 3 of the present invention.

The structure of the obtained white solid was identified by NMR. The $^1$H-NMR measurement result is presented in FIG. 3.

$^1$H-NMR (CDCl$_3$) detected 37 hydrogen signals, as follows.

δ (ppm)=7.21-8.00 (27H), 8.13 (2H), 8.19 (1H), 8.24 (1H), 8.51-8.95 (6H).

Example 4

Synthesis of [4'-[2-{3-(9H-carbazol-9-yl)phenyl}-9H-carbazol-9-yl]biphenyl-4-yl]-3,5-diphenyl-1,3,5-triazine (Compound 4)

To a reaction vessel having been substituted with nitrogen, 4'-bromobiphenyl-4-carboxylic acid (5.0 g), thionyl chloride (20 mL), and N,N-dimethylformamide were added and heated under refluxing for 1 hour. After distilling off thionyl chloride, the reaction mixture was allowed to cool, and dichloromethane (100 mL), benzonitrile (3.8 mL), and antimony(V) chloride (5.4 g) were added thereto, followed by heating under refluxing for 3 hours under stirring. After allowing the reaction mixture to cool to room temperature, an orange solid matter formed was collected by filtration. After rinsing the product with dichloromethane, the product was added gradually to aqueous ammonia (180 mL), and the mixture was stirred for 1 hour under cooling to 0° C. The product was collected by filtration, thereby providing a white solid matter of (4'-bromobiphenyl-4-yl)-3,5-diphenyl-1,3,5-triazine (yield: 53%).

(4'-Bromobiphenyl-4-yl)-3,5-diphenyl-1,3,5-triazine (1.0 g) thus obtained and 2-{3-(9H-carbazol-9-yl)phenyl}-9H-carbazole (0.88 g) synthesized in Example 1 were added to a reaction vessel having been substituted with nitrogen, to which tri-tert-butylphosphine (0.09 g), tert-butoxy sodium (0.23 g), and xylene (60 mL) were further added, and subsequently tris(dibenzylideneacetone) dipalladium chloroform inclusion complex (0.07 g) was further added, and the reaction mixture was heated under refluxing for 3 hours under stirring. After cooling to room temperature, a saturated sodium chloride aqueous solution (100 mL) and ethyl acetate (50 mL) were added thereto, and an organic layer was collected through extraction. After distilling off the solvent, the product was purified by column chromatography, thereby providing a white solid matter of [4'-[2-{3-(9H-carbazol-9-yl)phenyl}-9H-carbazol-9-yl]biphenyl-4-yl]-3,5-diphenyl-1,3,5-triazine (Compound 4) (yield: 42%).

[Chemical Formula 72]

(Compound 4)

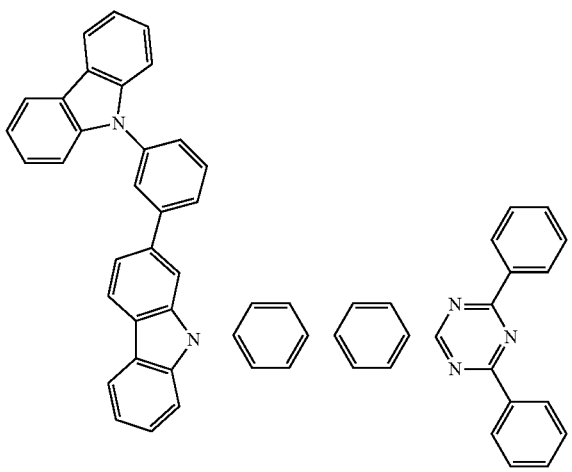

Figure 4:
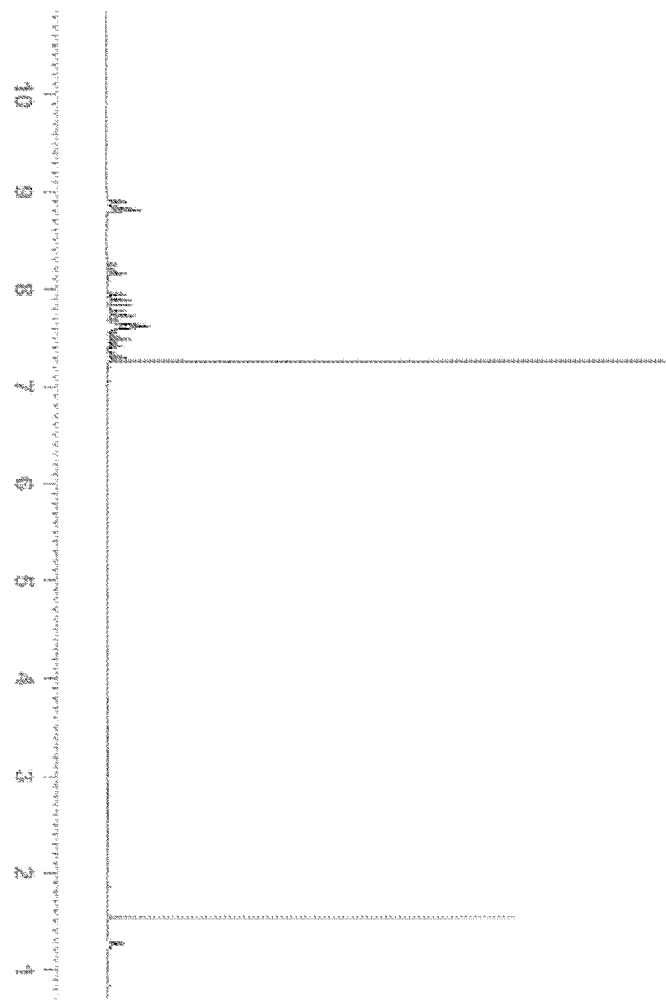
FIG. 4 is a $^1$H-NMR chart of the compound (compound 4) of Example 4 of the present invention.

The structure of the obtained white solid was identified by NMR. The $^1$H-NMR measurement result is presented in FIG. 4.

$^1$H-NMR (CDCl$_3$) detected 37 hydrogen signals, as follows.

δ (ppm)=7.21-8.00 (27H), 8.13 (2H), 8.19 (1H), 8.24 (1H), 8.51-8.95 (6H).

Example 5

A 100 nm-thick vapor-deposited film was fabricated on an ITO substrate using the compound of Example 1 (Compound 6). The work function was measured using an atmosphere photoelectron spectrometer (AC-3 produced by Riken Keiki Co., Ltd.).

|  | Work function |
| --- | --- |
| Compound of Example 1 | 6.10 eV |
| CBP | 6.00 eV |

As shown above, the compound having a carbazole ring structure represented by the general formula (1) has an energy level favorable as a material of a light emitting layer, which is equivalent to CBP, which has been ordinarily used as a light-emitting host material.

The compound has a larger work function than the work function of 5.4 eV of the ordinary hole transport materials, such as NPD and TPD, and thus has a large hole blocking capability.

Example 6

An ultraviolet-visible absorption spectrum of a thin film (100 nm) of the compound of Example 1 (Compound 6) has an absorption end of 355 nm, from which a band gap of 3.49 eV is calculated. Accordingly, an electron affinity of 2.61 eV is calculated for the compound of Example 1 (Compound 6) from the value of the work function (6.10 eV).

As shown above, the compound having a carbazole ring structure represented by the general formula (1) has a smaller electron affinity than the electron affinity of 2.7 eV of the ordinary electron transport materials, such as TPBi, and thus is understood to be excellent in electron injection property.

Example 7

On a glass substrate, the compound of Example 1 (Compound 6) and 2,4,5,6-9H-tetracarbazolyl-9-yl-dicyanobenzene (4CzIPN) shown by the following structural formula were subjected to dual vapor deposition at a vapor deposition rate providing a vapor deposition rate ratio of (compound of Example 1 (Compound 6))/(4CzIPN) of 94/6, so as to produce a thin film having a thickness of 100 nm, which was designated as an organic photoluminescent (PL) device. The device was measured with Absolute PL quantum yield spectrometer, Quantaurus-QY, produced by Hamamatsu Photonics K.K., under nitrogen steam at 300 K, and the PL quantum efficiency thereof was 57%.

[Chemical Formula 73]

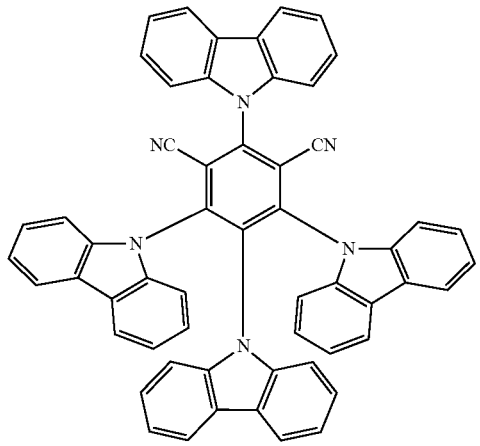

(4CzIPN)

Example 8

Figure 5:
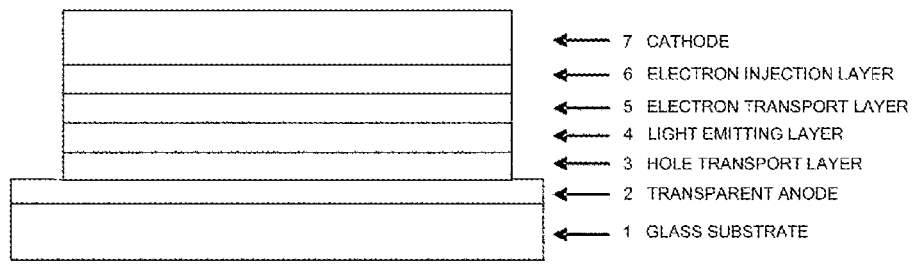
FIG. 5 is a diagram illustrating the configuration of the EL devices of Example 8 and Comparative Example 1.

An organic EL device was fabricated by vapor-depositing a hole transport layer 3, a light emitting layer 4, an electron transport layer 5, an electron injection layer 6, and a cathode (aluminum electrode) 7 in this order on a glass substrate 1 on which an ITO electrode was formed as a transparent anode 2 beforehand, as shown in FIG. 5.

Specifically, the glass substrate 1 having ITO (a thickness of 100 nm) formed thereon was washed with an organic solvent, and subjected to a UV ozone treatment to wash the surface. The glass substrate with the ITO electrode was then installed in a vacuum vapor deposition apparatus, and the pressure was reduced to 0.001 Pa or less.

Subsequently, NPD was formed to a thickness of 35 nm as the hole transport layer 3 to cover the transparent anode 2. On the hole transport layer 3, the compound of Example 1 (Compound 6) and 4CzIPN of the aforementioned structural formula were subjected to dual vapor deposition at a vapor deposition rate providing a vapor deposition rate ratio of (Compound of Example 1 (Compound 6))/(4CzIPN) of 95/5 to a thickness of 15 nm as the light emitting layer 4. On the light emitting layer 4, TPBI was formed to a thickness of 65 nm as the electron transport layer 5. On the electron transport layer 5, lithium fluoride was formed to a thickness of 0.8 nm as the electron injection layer 6. Finally, aluminum was vapor-deposited to a thickness of 70 nm to form the cathode 7. The characteristics of the organic EL device were measured in the atmosphere at ordinary temperature.

Table 1 summarizes the results of the emission characteristics measurements after applying DC voltage to the organic EL device fabricated with the compound of Example 1 (Compound 6).

Comparative Example 1

For comparison, an organic EL device was fabricated under the same conditions as in Example 8 except that CBP was used as the material of the light emitting layer 4 instead of the compound of Example 1 (Compound 6), and the materials were subjected to dual vapor deposition at a vapor deposition rate providing a vapor deposition rate ratio of (CBP)/(4CzIPN) of 95/5 to a thickness of 15 nm. The characteristics of the organic EL device were measured in the atmosphere at ordinary temperature. Table 1 summarizes the results of the emission characteristics measurements after applying DC voltage to the organic EL device.

TABLE 1

| Compound | Voltage [V] (@10 mA/cm$^2$) | Luminance [cd/m$^2$] (@10 mA/cm$^2$) | Power efficiency [lm/W] (@10 mA/cm$^2$) |
|---|---|---|---|
| Ex. 8 Compound 6 | 6.6 | 1168 | 11.1 |
| Com. Ex. 1 CBP | 7.8 | 799 | 6.6 |

As shown in Table 1, the driving voltage on application of an electric current of a current density of 10 mA/cm$^2$ was 7.8 V for the organic EL device of Comparative Example 1 using CBP, but was lowered to 6.6 V for the organic EL device of Example 8 using the compound of Example 1 (Compound 6). The luminance on application of an electric current of a current density of 10 mA/cm$^2$ was 799 cd/m$^2$ for the organic EL device of Comparative Example 1 using CBP, but was largely enhanced to 1,168 cd/m$^2$ for the organic EL device of Example 8 using the compound of Example 1 (Compound 6). The power efficiency was 6.6 lm/W for the organic EL device of Comparative Example 1 using CBP, but was largely enhanced to 11.1 lm/W for the organic EL device of Example 8 using the compound of Example 1 (Compound 6).

It was thus understood that the organic EL device of the present invention was excellent in driving voltage, luminance, and power efficiency, as compared to the device using CBP, which was used as an ordinary light-emitting material (host material).

As described above, the compound having a carbazole ring structure represented by the general formula (1) has a favorable energy level, is excellent in electron injection property, has a large hole blocking capability, and thus has a favorable capability of confining triplet energy.

INDUSTRIAL APPLICABILITY

The compound having a carbazole ring structure represented by the general formula (1) has a favorable energy level and a favorable capability of confining triplet energy, and thus is excellent as a host compound of a light emitting

The invention claimed is:

1. An organic electroluminescent device comprising a pair of electrodes and one layer or plural layers including at least a light emitting layer intervening between the electrodes, the light emitting layer containing as a host material thereof a light-emitting material comprising a compound having a carbazole ring structure represented by the following general formula (1):

[Chemical Formula 1]

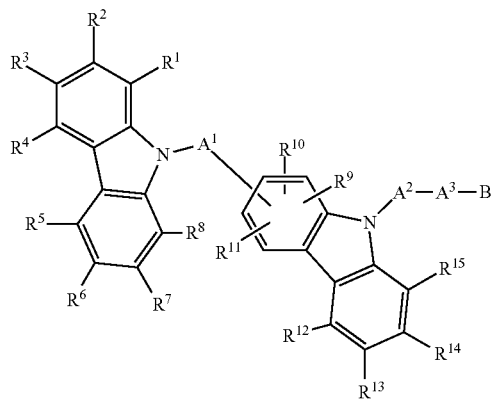

(1)

wherein $A^1$ and $A^2$ may be the same or different, and each represents a divalent group of a substituted or unsubstituted aromatic hydrocarbon or a divalent group of a substituted or unsubstituted condensed polycyclic aromatics;

$A^3$ represents a divalent group of a substituted or unsubstituted aromatic hydrocarbon, a divalent group of a substituted or unsubstituted condensed polycyclic aromatics, or a single bond; B represents a substituted or unsubstituted pyridyl, bipyridyl, terpyridyl, pyrimidinyl, pyrazinyl, pyridazinyl, triazinyl, pyrrolyl, pyrazolyl, imidazolyl, triazolyl, oxazolyl, isoxazolyl, thiazolyl, isothiazolyl, oxadiazolyl, thiadiazolyl, furyl, thienyl, quinolyl, isoquinolyl, quinoxalinyl, quinazolinyl, naphthyridinyl, indolyl, isoindolyl, benzoimidazolyl, benzotriazolyl, benzofuranyl, benzothienyl, benzoxazolyl, benzoxadiazolyl, benzothiazolyl, benzothiadiazolyl, pyridopyrrolyl, pyridoimidazolyl, pyridotriazolyl, pteridinyl, acridinyl, phenazinyl, phenanthrolinyl, phenoxazinyl, phenothiazinyl, phenocelenazinyl, phenotellurazinyl, phenophosphinazinyl, carbolinyl, dibenzofuranyl, dibenzothienyl, or xanthenyl;

and $R^1$ to $R^{15}$ may be the same or different, and each represents a hydrogen atom, a deuterium atom, a fluorine atom, a chlorine atom, cyano, nitro, linear or branched alkyl of 1 to 20 carbon atoms that may have a substituent, cycloalkyl of 5 to 10 carbon atoms that may have a substituent, linear or branched alkenyl of 2 to 20 carbon atoms that may have a substituent, linear or branched alkyloxy of 1 to 20 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, a substituted or unsubstituted aryloxy group, or a disubstituted amino group substituted with an aromatic hydrocarbon group, an aromatic heterocyclic group, or a condensed polycyclic aromatic group, and may bind to each other via a single bond, a substituted or unsubstituted methylene, an oxygen atom, or a sulfur atom, to form a ring and wherein the organic electroluminescent device emits delayed fluorescence.

2. The organic electroluminescent device according to claim 1, wherein in the general formula (1), $A^1$ represents phenylene.

3. The organic electroluminescent device according to claim 1, wherein in the general formula (1), $A^2$ represents phenylene.

4. The organic electroluminescent device according to claim 1, wherein in the general formula (1), $A^3$ represents phenylene.

5. The organic electroluminescent device according to claim 2, wherein in the general formula (1), $A^3$ represents phenylene.

6. The organic electroluminescent device according to claim 3, wherein in the general formula (1), $A^3$ represents phenylene.

7. The organic electroluminescent device according to claim 1, wherein in the general formula (1), $A^3$ represents a single bond.

8. The organic electroluminescent device according to claim 2, wherein in the general formula (1), $A^3$ represents a single bond.

9. The organic electroluminescent device according to claim 3, wherein in the general formula (1), $A^3$ represents a single bond.

10. The organic electroluminescent device according to claim 1, wherein in the general formula (1), $A^3$ represents biphenylene.

11. The organic electroluminescent device according to claim 2, wherein in the general formula (1), $A^3$ represents biphenylene.

12. The organic electroluminescent device according to claim 3, wherein in the general formula (1), $A^3$ represents biphenylene.

* * * * *